United States Patent
Martin

(10) Patent No.: US 11,937,890 B2
(45) Date of Patent: Mar. 26, 2024

(54) DIRECT DRIVE FOR MECHANICAL ARM ASSEMBLY

(71) Applicant: Intuitive Surgical Operations, Inc., Sunnyvale, CA (US)

(72) Inventor: David F. Martin, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 539 days.

(21) Appl. No.: 17/097,612

(22) Filed: Nov. 13, 2020

(65) Prior Publication Data

US 2021/0145530 A1  May 20, 2021

Related U.S. Application Data

(60) Provisional application No. 62/935,586, filed on Nov. 14, 2019.

(51) Int. Cl.
*B25J 9/10* (2006.01)
*A61B 34/00* (2016.01)
(Continued)

(52) U.S. Cl.
CPC .............. *A61B 34/35* (2016.02); *A61B 34/71* (2016.02); *A61B 90/10* (2016.02); *A61B 2034/715* (2016.02); *B25J 9/1045* (2013.01)

(58) Field of Classification Search
CPC ... A61B 34/35; A61B 34/71; A61B 2034/715; B25J 9/106; B25J 9/1045; B25J 9/0048; B25J 9/042; B25J 9/041
See application file for complete search history.

(56) References Cited

U.S. PATENT DOCUMENTS 6,318,951 B1 * 11/2001 Schmidt .................... B25J 5/02
  414/935
6,587,750 B2  7/2003 Gerbi et al.
(Continued)

FOREIGN PATENT DOCUMENTS

JP  2019063933 A * 4/2019 .............. B25J 13/06
KR  20120139534 A * 12/2012 .............. B25J 13/06
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Bobby Rushing, Jr.
(74) *Attorney, Agent, or Firm* — IP Spring

(57) ABSTRACT

Implementations relate to a direct drive for a mechanical arm assembly. In some implementations, a mechanical arm assembly includes a base member, a first arm member rotatably coupled to the base member at a first portion of the first arm member, and a second arm member having a first portion rotatably coupled to a second portion of the first arm member. The first arm member is rotatable with respect to the base member about a first axis, and the second arm member is rotatable with respect to the first arm member about a second axis. A first motor coupled to the base member, the first motor including a first drive shaft rotatable about the first axis and coupled to the first arm member. A grip member is coupled to a second portion of the second arm member.

16 Claims, 10 Drawing Sheets

(51) Int. Cl.
 *A61B 34/35* (2016.01)
 *A61B 90/10* (2016.01)

(56) References Cited

U.S. PATENT DOCUMENTS

| | | | |
|---|---|---|---|
| 6,714,839 B2 | 3/2004 | Salisbury, Jr. et al. | |
| 7,975,568 B2 * | 7/2011 | Zhang | B25J 9/042 |
| | | | 901/19 |
| 8,073,335 B2 | 12/2011 | Labonville et al. | |
| 8,511,198 B2 * | 8/2013 | Zhang | B25J 9/102 |
| | | | 74/665 GE |
| 8,777,547 B2 * | 7/2014 | Kremerman | B65G 47/904 |
| | | | 414/217 |
| 10,155,309 B1 * | 12/2018 | Blank | H01L 21/68707 |
| 10,449,011 B2 * | 10/2019 | Coooper | A61B 34/71 |
| 2006/0099063 A1 * | 5/2006 | Pietrantonio | B25J 9/042 |
| | | | 414/744.5 |
| 2010/0196220 A1 * | 8/2010 | Bria | F23G 7/068 |
| | | | 422/171 |
| 2019/0321112 A1 * | 10/2019 | Cecil | A61B 90/37 |

FOREIGN PATENT DOCUMENTS

| | | | | |
|---|---|---|---|---|
| WO | WO-2012010042 A1 * | 1/2012 | | F16H 1/166 |
| WO | WO-2017210073 A1 | 12/2017 | | |

\* cited by examiner

DIRECT DRIVE FOR MECHANICAL ARM ASSEMBLY

CROSS-REFERENCE TO RELATED APPLICATIONS

The present application claims priority to U.S. Provisional Patent Application No. 62/935,586, filed Nov. 14, 2019 and titled "Direct Drive for Mechanical Arm Assembly," the entire contents of which is hereby incorporated by reference.

BACKGROUND

Control input devices allow a user to control functions of various types of mechanisms and instruments. For example, control input devices can be used in teleoperated systems such as teleoperated surgical devices that use various types of medical instruments to perform minimally invasive surgical procedures that reduce damage to healthy tissue of patients. The medical instruments can be connected to controlled manipulator devices such as manipulator arms that can be manipulated to perform the surgical procedures. Control of the medical instruments of a manipulator device can be provided to an operator at one or more control input devices, e.g., at a remote terminal or station. Actuators of the manipulator device can be controlled by the control input device to cause motion or initiate a function of a medical instrument, camera, or other end effector at the manipulator device that interacts with the patient surgical site. Other teleoperated systems can also make use of control input devices to allow a user to control one or more manipulator devices at a work site.

In some examples, the control input device can be physically manipulated by the user in one or more degrees of freedom to perform functions of a manipulator device, e.g., control an end effector to be moved in coordination with the manipulation of the control input device and in corresponding degrees of freedom at the work site. In some cases, the degrees of freedom are provided using a mechanical arm, e.g., mechanical linkage, of the control input device. For example, members of the arm can be rotatably coupled between a handle of the control input device and a support or ground.

In some control implementations, forces are output on the control input device from motors attached to the mechanical arm. The forces can provide force feedback to the control input device in one or more of its degrees of freedom. In some cases, the forces can provide gravity compensation to the control input device, allowing easier movement of the control input device by a user. In additional examples, the forces can provide simulated interactions to the control input device that correspond to interactions of controlled manipulator instruments at the work site. For example, a motor can output a torque that is applied to a rotational joint between two links of the arm coupled to the control input device, or can drive a transmission mechanism connected between the motor and a link of the arm that transfers torque to the link.

The motors used to provide force feedback to a control input device or other device via a mechanical arm are often small in order to reduce the cost of the device. Thus, transmissions including gear reduction are commonly used to scale output torques to higher magnitudes. For example, a gear mechanism or capstan mechanism may be used to scale output torques from motors. However, such mechanisms add additional costs and assembly complexity to control input devices and their support mechanisms. Furthermore, such transmissions may scale up particular operating characteristics of a motor, such as friction and or torque disturbances (ripple), that are desired to be reduced or minimized to achieve more smooth and realistic operation and force feedback at the control input device.

SUMMARY

Implementations of the present application relate to a direct drive for a mechanical arm assembly. In some implementations, a mechanical arm assembly includes a base member and a first arm member that includes a first portion and a second portion, the first arm member being rotatably coupled to the base member at the first portion of the first arm member, and the first arm member being rotatable with respect to the base member about a first axis. The mechanical arm assembly includes a first motor coupled to the base member, the first motor including a first drive shaft rotatable about the first axis and coupled to the first arm member. The mechanical arm assembly includes a second arm member including a first portion and a second portion, the first portion of the second arm member being rotatably coupled to the second portion of the first arm member, and the second arm member being rotatable with respect to the first arm member about a second axis. The mechanical arm assembly also includes a grip member coupled to the second portion of the second arm member.

Various implementations and examples of the mechanical arm assembly are described. For example, in some implementations, the first portion of the first arm member is a first end of the first arm member, the second portion of the first arm member is a second end of the first arm member, the first portion of the second arm member is a first end of the second arm member, and the second portion of the second arm member is a second end of the second arm member. In some implementations, the first motor is configured to rotate the first drive shaft and output torque on the first arm member about the first axis. In some implementations, a 1:1 drive ratio of torque is provided from the first motor to the first arm member. In some implementations, the first drive shaft is directly coupled to the first arm member.

In some implementations, the second axis is parallel to the first axis, the mechanical arm assembly further includes a second motor coupled to the base member, and the second motor includes a second drive shaft rotatable about the first axis and coupled to the second arm member. In some implementations, a first sensor is coupled to the first drive shaft, and a second sensor is coupled to the second drive shaft. The second motor can be configured to rotate the second drive shaft and output torque on the second arm member as torque about the second axis. In some implementations, the mechanical arm assembly further includes a force transmission mechanism coupled between the second drive shaft and the second arm member. For example, the force transmission mechanism can include a drive pulley and a tension element, the drive pulley being coupled to the second drive shaft and the tension element being coupled between the drive pulley and the second arm member. In some examples, the tension element extends along a length of the first arm member and is coupled to a second pulley, and the second pulley is coupled to the tension element and to the second arm member and is rotatable about the second axis. In some implementations, a 1:1 drive ratio of torque is provided from the second motor to the second arm member.

In some implementations, the base member is rotatable about a third axis that is orthogonal to the first axis, and the mechanical arm assembly further includes a third motor coupled to a support, the third motor including a third drive shaft rotatable about the third axis and coupled to the base member. The third motor can be configured to rotate the third drive shaft and output torque on the base member about the third axis. In some implementations, a 1:1 drive ratio of torque is provided from the third motor to the base member. In some implementations of the mechanical arm assembly, the grip member is movable in one or more degrees of freedom provided by rotation of the first arm member and the second arm member about the first and second axes, respectively. In some implementations, the mechanical arm assembly is included in a teleoperated surgical system.

In some implementations, a mechanical arm assembly includes a base member and a first arm member, the first arm member including a first portion and a second portion and being rotatably coupled to the base member at the first portion of the first arm member, and the first arm member being rotatable with respect to the base member about a first axis. The arm assembly includes a first motor coupled to the base member, the first motor including a first drive shaft coupled to the first arm member, the first drive shaft being rotatable about an axis of rotation. The arm assembly includes a second arm member that includes a first portion and a second portion, the first portion of the second arm member being rotatably coupled to the second portion of the first arm member, and the second arm member being rotatable about a second axis that extends parallel to the first axis. The arm assembly includes a second motor coupled to the base member, the second motor including a second drive shaft rotatable about the axis of rotation of the first drive shaft, and the second drive shaft being coupled to the second arm member. The arm assembly includes a first rotary sensor coupled to the first drive shaft and configured to detect an orientation of the first arm member about the first axis, and a second rotary sensor coupled to the second drive shaft and configured to detect an orientation of the second arm member about the second axis. A grip member is coupled to the second portion of the second arm member and movable in one or more degrees of freedom provided by rotation of the first arm member or the second arm member.

In some implementations, the first axis is the same as the axis of rotation of the first drive shaft, the base member is rotatable about a third axis orthogonal to the first axis, and the control input device further includes a third motor coupled to a support, the third motor including a third drive shaft rotatable about the third axis and coupled to the base member. In some implementations, the mechanical arm assembly further includes a force transmission mechanism coupled between the second drive shaft and the second arm member, the force transmission mechanism including a drive pulley coupled to the second drive shaft and a tension element coupled between the drive pulley and the second arm member In some implementations, a mechanical arm assembly includes base member means and first arm means for rotating about a first axis, the first arm means rotatably coupled to the base member means at a first portion of the first arm means. The mechanical arm assembly includes means for outputting a first torque on the first arm means about the first axis using a first drive shaft rotatable about the first axis, the first drive shaft coupled to the first arm means. The arm assembly includes second arm means for rotating about a second axis, the second arm means having a first portion rotatably coupled to a second portion of the first arm means, the second axis extending parallel to the first axis. The arm assembly includes means for outputting a second torque on the second arm means about the second axis using a second drive shaft rotatable about the first axis, the second drive shaft coupled to the second arm means. The arm assembly includes means for receiving a grip of a user, the means for receiving a grip being coupled to the second arm means and moveable in one or more degrees of freedom provided by rotation of the first arm means and the second arm means.

In some implementations, a method includes receiving a first control signal at a first motor coupled to an arm mechanism, the first motor including a first drive shaft rotatable about a first axis, and the arm mechanism including a base member, a first arm member rotatably coupled to the base member and rotatable about the first axis, and a second arm member rotatably coupled to the first arm member and rotatable about a second axis. The method includes outputting a first torque on the first arm member about the first axis using the first drive shaft of the first motor based on the first control signal and receiving a second control signal at a second motor coupled to the arm mechanism, the second motor including a second drive shaft. The method includes outputting a second torque on the second arm member about a second axis using the second drive shaft of the second motor based on the second control signal.

DETAILED DESCRIPTION

Figure 1:
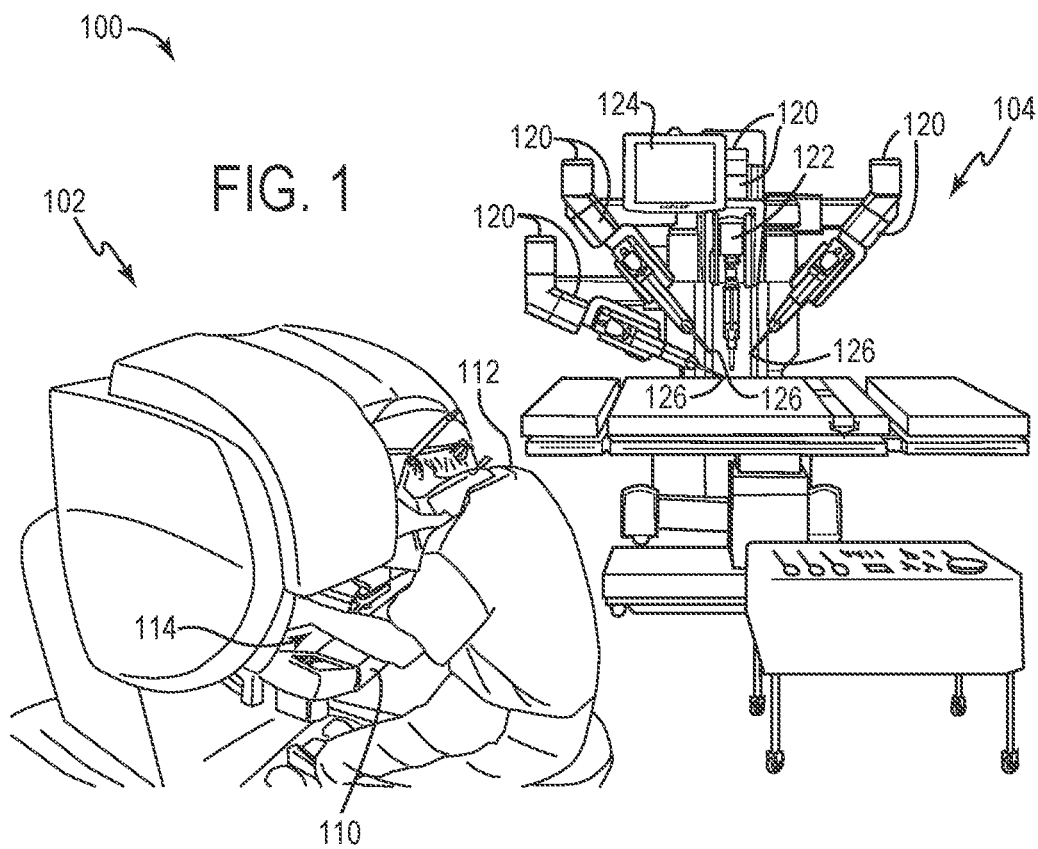
FIG. 1 is a diagrammatic illustration of an example implementation of a teleoperated surgical system which can be used with one or more features disclosed herein, according to some implementations.

One or more implementations described herein relate to a direct drive for a mechanical arm assembly, e.g., of a control input device or other input device. In some implementations, a mechanical arm assembly includes a base member, a first arm member rotatably coupled to the base member about a first axis, and a second arm member rotatably coupled to the first arm member about a second axis that, for example, extends parallel to the first axis. A first motor is coupled to the base member and includes a first drive shaft that extends along the first axis and is coupled to the first arm member. A grip member is coupled to the second arm member which can be grasped or contacted by a user to, for example, move the grip member in space and provide corresponding control signals to a control circuit. The drive shaft of the first motor rotates about the axis of rotation of the first arm member, so that the first motor can directly drive the first arm member about its axis of rotation. For example, no torque scaling is applied for the torque output of the first arm motor on the first arm member.

Various other features are also disclosed. For example, a second motor can be coupled to the base member and includes a second drive shaft that is rotatable about the first axis and is coupled to the second arm member. The second motor can apply torque to the second arm member. In some examples, a force (e.g., torque) transmission mechanism can be coupled between the second drive shaft and the second arm member, e.g., a drive pulley and a tension member such as a belt that extends along the length of the first arm member to the second arm member. For example, no torque scaling is applied to the torque output of the second arm motor on the second arm member. In further examples, the base member is rotatable about a third axis that, e.g., is orthogonal to the first axis, and a third motor is coupled to a support and includes a third drive shaft that extends along the third axis and is coupled to the base member. For example, no torque scaling is applied to the torque output of the third motor on the base member. Each of the three motors can individually apply torque to its associated coupled member.

Features described herein provide a driven mechanical arm assembly with several advantages. For example, one or more motors are connected to associated members of the arm assembly, e.g., with a drive shaft aligned to rotate about the axis of rotation of the driven member or pulley. This allows the motors to output torque on the arm members or pulley without torque scaling and thus without amplification of undesirable attributes such as motor friction and or torque disturbances (ripple), thereby providing forces having greater fidelity to specified or simulated forces output to a user of the arm assembly. The use of a direct drive motor allows a scaling mechanism (such as a gear mechanism or capstan mechanism) to be omitted, thus avoiding additional friction introduced by such a mechanism and saving cost and assembly time of the mechanical arm assembly. For example, this feature can avoid the assembly of a complex capstan mechanism that includes cables and several drum components. In addition, the arm is configured to allow multiple drive motors to be manufactured as a substantially identical type of motor, allowing duplication of parts and less-costly manufacture. Furthermore, the motor configurations described here allow for a more compact and smaller packaging of the arm assembly and fewer obstructions to vision of a user operating a control input device coupled to the arm assembly. Furthermore, some implementations provide motors that are facing opposite directions and have their drive shafts aligned with the axis of rotation of a first arm member, which provides balanced weight on the base member, reduced inertia for the first and second arm members, and/or allows the second arm member to be moved using a tension element coupled between the drive shaft of a motor and the second arm member.

The terms "center," "parallel," "perpendicular," "orthogonal," "aligned," or particular measurements in degrees, Hertz, or other units as used herein need not be exact and can include typical engineering tolerances. Some implementations herein may relate to various objects in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As referred to herein, a mechanically grounded unit or device is constrained with respect to possible position and orientation motion in a large working environment (e.g., an operating area or room). Also, such a unit is kinematically coupled to the ground (e.g., mechanically supported by a console, supports, or other object attached to the ground). As used herein, the term "proximal" refers to an element that is close to (or closer to) a mechanical ground and the term "distal" refers to an element that is away from (or further from) a mechanical ground.

The term "torque" as used herein refers to rotational forces and/or refers to a context of rotational motion, and in various implementations using one or more described features, other types of forces can be used as appropriate in place of or in addition to torque, e.g., linear forces or other forces, and/or forces in a context of translational motion. The term "finger," as used herein, refers to any digit of the hand, e.g., thumb, index finger, middle finger, ring finger, or pinky finger.

FIG. 1 is a diagrammatic illustration of an example teleoperated surgical system 100 which can be used with one or more features disclosed herein. Other types of control systems and/or master-slave systems can be used in other implementations involving described features. Teleoperated surgical system 100 includes a user control system (e.g., surgeon's console or workstation) 102 and a manipulator system 104.

In this example, the user control system 102 includes a viewer 213 (shown in FIG. 2) where an image of a worksite is displayed during an operating procedure using the system 100. For example, the image can be displayed by a display device such as one or more display screens, depict a surgical site during a surgical procedure. A support 110 is provided on which a user 112, e.g., an operator such as a surgeon, can rest his or her forearms while gripping two control input devices 210 and 212 (examples shown in FIG. 2), one in each hand. The control input devices are positioned in a workspace 114 disposed inwardly beyond the support 110. When using the workstation 102, the user 112 can sit in a chair in front of the workstation, position his or her eyes in front of the viewer 213 and grip the control input devices, one in each hand, while resting his or her forearms on the support 110. Additional details are described below with reference to FIG. 2.

A manipulator system 104 is also included in the teleoperated system 100. For example, manipulator system 104 can be a manipulator device in this example, or can alternatively be a different type of controlled device. In some implementations as shown, during a surgical procedure, the manipulator system 104 can be positioned close to a patient for surgery at a surgical site (or close to other worksite), and its base can remain stationary until a particular surgical procedure or stage of a procedure is completed. Manipulator system 104 can include one or more manipulator arm assemblies 120. In some examples, one or more of the arm assemblies 120 can be configured to hold an image capturing device, e.g., an endoscope 122, which can provide captured images of a portion of the surgical site. In some implementations, the captured images can be transmitted to viewer 213 of the workstation 102 and/or transmitted to one or more other displays, e.g., a display 124 coupled to the manipulator system 104. In some examples, each of the other arm assemblies 120 may include a surgical tool 126. Each surgical tool 126 can include a surgical end effector, e.g., for treating tissue of the patient. For example, an arm assembly 120 can include one or more motors or other actuators that operate associated features of the end effector, such as the pitch, yaw, and/or roll of the end effector, opening jaws or moving a blade of the end effector, the output of material transported through a connecting tube (e.g., liquid or other fluids), suction forces, and/or any of a multiple of other end effector functions. One example of a surgical manipulator arm is a da Vinci® surgical system instrument manipulator arm in surgical systems commercialized by Intuitive Surgical Operations, Inc. of Sunnyvale, California.

In this example, the arm assemblies 120 can be caused to move and articulate the surgical tools 126 in response to manipulation of the control input devices 210 and 212 at the workstation 102 by the user 112, e.g., so that the user 112 can direct surgical procedures at internal surgical sites through minimally invasive surgical apertures. For example, one or more actuators coupled to the arm assemblies 120 can output torque to cause links or other portions of the arm assemblies to move in particular degrees of freedom in response to control signals received from the workstation 102. For example, movement of an arm and end effector in one or more degrees of freedom can correspond to (e.g., follow) movement in one or more degrees of freedom of an associated control input device handle by a user. The workstation 102 can be used within a room (e.g., an operating room) with the manipulator system 104 or can be positioned more remotely from the manipulator system 104, e.g., at a different location than the manipulator device.

Some implementations of the teleoperated system 100 can provide different modes of operation. In some examples, in a non-controlling mode (e.g., safe mode) of the teleoperated system 100, the controlled motion of the manipulator system 104 is disconnected from the control input devices of the user control system 102 in disconnected configuration, such that movement and other manipulation of the control input devices does not cause motion of the manipulator system 104. In a controlling mode of the teleoperated system (e.g., following mode, in which one or more manipulator arms (or other elements) follow the movements of a corresponding control input device), motion of the manipulator system 104 can be controlled by the control input devices 210 and 212 of the workstation 102 such that movement and other manipulation of the control input devices causes motion of the manipulator system 104, e.g., during a surgical procedure.

Some implementations can be or include a teleoperated medical system such as a da Vinci® Surgical System (e.g., a Model IS3000 or IS4000, marketed as the da Vinci Si® or da Vinci Xi® Surgical System), commercialized by Intuitive Surgical, Inc. of Sunnyvale, California Features disclosed herein may be implemented in various ways, including in implementations at least partially computer-controlled, controlled via electronic control signals, manually controlled via direct physical manipulation, etc. Implementations on da Vinci® Surgical Systems are merely exemplary and are not to be considered as limiting the scope of the features disclosed herein. For example, different types of teleoperated systems having manipulator devices at worksites can make use of actuated controlled features described herein. Other, non-teleoperated systems can also use one or more described features, e.g., various types of control systems and devices, peripherals, etc.

In some implementations, a controlled manipulator device can be a virtual representation of device, e.g., presented in a graphical simulation provided by a computing device coupled to the teleoperated system 100. For example, a user can manipulate the control input devices 210 and 212 of the workstation 102 to control a displayed representation of an end effector in virtual space of the simulation, similarly as if the end effector were a physical object coupled to a physical manipulator device.

Figure 2:
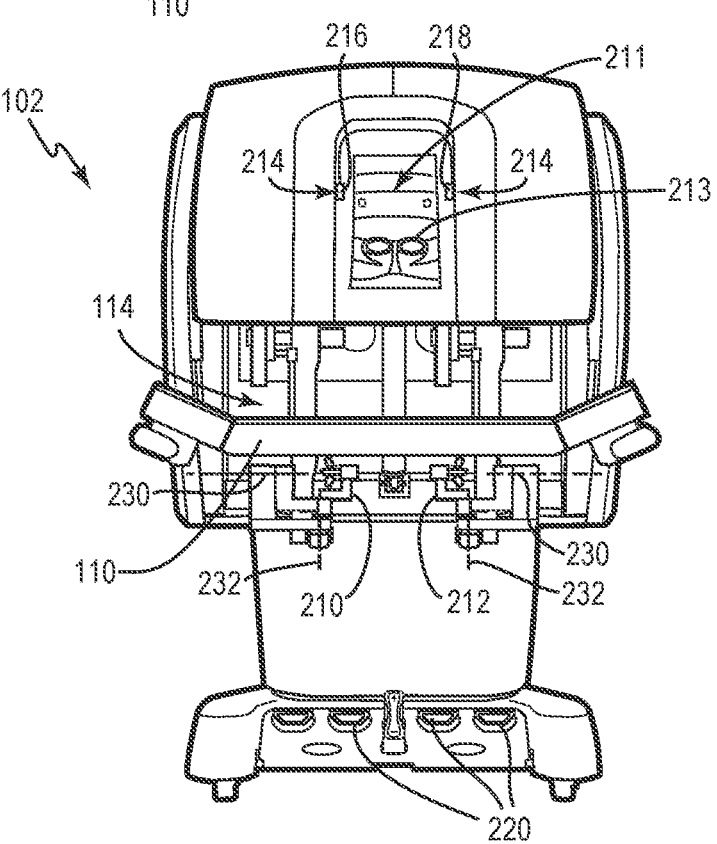
FIG. 2 is a front elevational view of an example user control system as shown in FIG. 1, according to some implementations.

FIG. 2 is a front elevational view of an example user control system 102 as described above for FIG. 1. User control system 102 includes a viewer 213, and an image of a worksite can be displayed in viewer 213 during a procedure using the teleoperated system 100. For example, images depicting a surgical site can be displayed during a surgical procedure. The viewer 213 can be positioned within a viewing recess 211 in which the user can position his or her head to view images displayed by the viewer 213. When using the workstation 102, the user 112 can sit in a chair in front of the workstation and position his or her head within the recess 211 such that the user's eyes are positioned in front of the viewer 213.

In some implementations, one or more user presence sensors 214 can be positioned at one or more locations of the user control system 102 to detect the presence of a user located next to or near to the workstation 102. In this example, the user presence sensors 214 can sense a presence of a user's head within the recess 211. For example, an optical sensor can be used for a presence sensor, the optical sensor including an emitter 216 and a detector 218. A beam of infrared or other wavelength of light is emitted from one side of the recess 211 by the emitter 216, and the beam is detected on the other side of the recess by the detector 218. If the beam is interrupted from detection by the detector, the system (e.g., a control circuit) determines that a user's head is within the recess and that the user is in a proper position to use the control input devices of the user control system 102. Additional or alternative types of presence sensors can be used in various implementations.

Two control input devices 210 and 212 are provided for user manipulation. In some implementations, each control input device 210 and 212 can be configured to control motion and functions an associated arm assembly 120 of the manipulator system 104. In some examples, the control input devices are master devices and manipulator system 104 is a slave device in a master-slave control relationship. For example, a control input device 210 or 212 can be moved in a plurality of degrees of freedom to move a corresponding end effector of the manipulator system 104 in corresponding degrees of freedom. The control input devices 210 and 212 are positioned in workspace 114 inwardly beyond the support 110. For example, a user 112 can rest his or her forearms while gripping the two control input devices 210, 212, with one control input device in each hand. The user also positions his or her head within the viewing recess 211 to view the viewer 213 as described above while manipulating the control input devices 210 and 212. The control input devices may include one or more of any number of a variety of input devices manipulable by the user, such as kinematically linked (mechanically grounded) hand grips, finger grips, joysticks, trackballs, data gloves, trigger-guns, hand-operated controllers, voice recognition devices, touch screens, and the like. Some examples of control input devices that can be used as control input devices 210 and 212 are described below with respect to FIG. 10.

In some implementations, the control input devices are manual input devices which move in all six Cartesian degrees of freedom, including motion about axes 230 and 232. Control input devices 210 and 212 may also include an actuatable grip portion (e.g., handle) for actuating corresponding instruments of a manipulator system, e.g., for closing grasping jaws, applying an electrical potential to an electrode, delivering a medicinal treatment, and the like. In some implementations, a grip function, such as moving two grip portions of a control input device together and apart in a pincher movement, can provide an additional mechanical degree of freedom (i.e., a grip DOF). In some example implementations, control input devices 210 and 212 may provide control of one or more surgical instruments 126 in a surgical environment or proxy surgical instruments in a virtual environment.

Some implementations of workstation 102 can include one or more foot controls 220 positioned below the control input devices 210 and 212. The foot controls 220 can be depressed, slid, and/or otherwise manipulated by a user's feet to input various commands to the teleoperated system while the user is operating the user control system 102.

Figure 3:
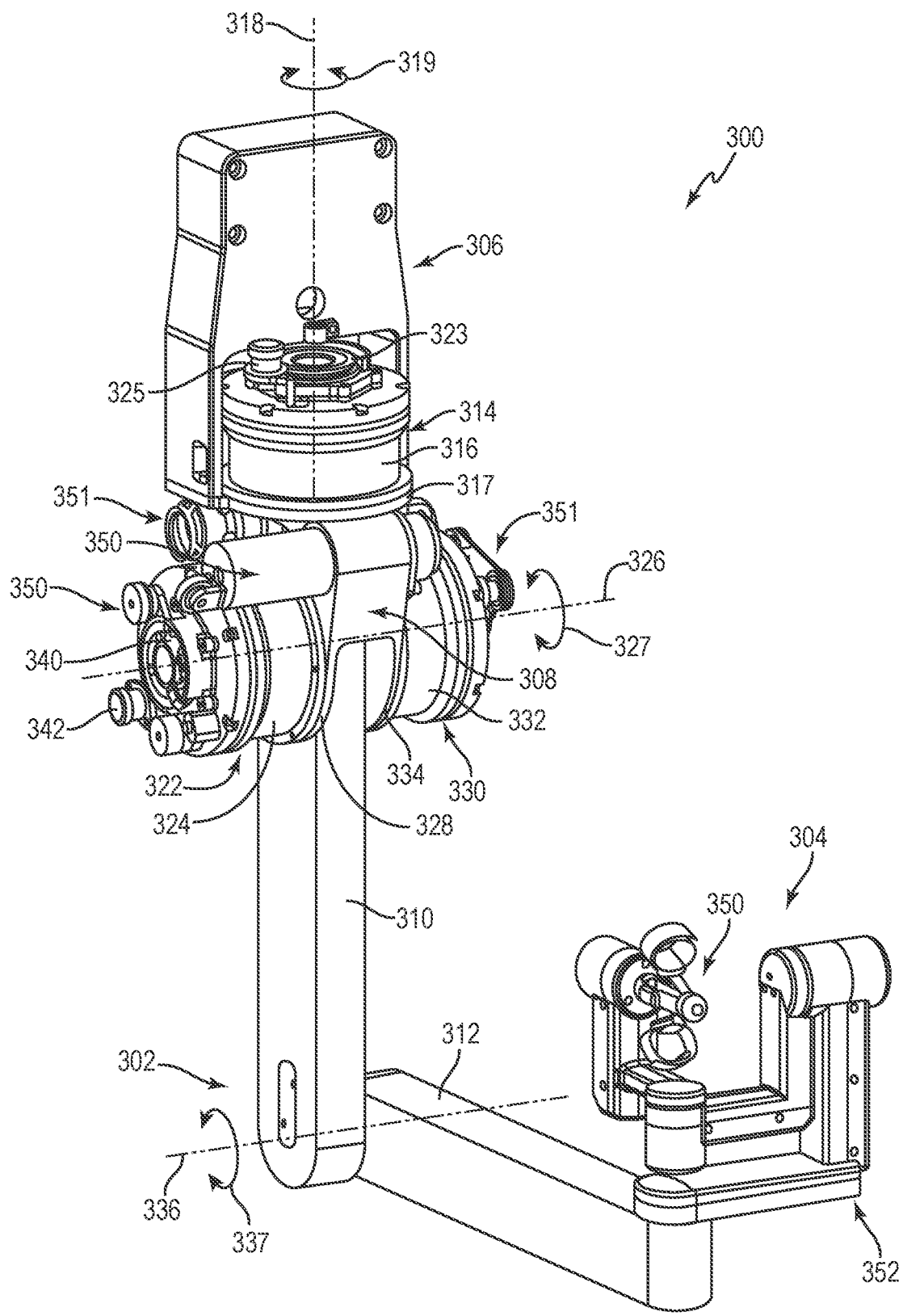
FIG. 3 is a perspective view of an example arm assembly which can include one or more features described herein, according to some implementations.

FIG. 3 is a perspective view of an example mechanical arm assembly 300 which can include one or more features described herein, according to some implementations. In some implementations, arm assembly 300 can be coupled to or included in a control input device, e.g., embodied or included in a user control system 102 as shown in FIGS. 1-2, or can be coupled to and used in a different device or support frame.

Arm assembly 300 includes an arm 302 and a control input device 304. Arm 302 includes multiple linked members that are each coupled to one or more other linked members of the arm 300, thus forming a linkage. In some implementations, as shown, arm 302 includes a base member 308, a first arm member 310, and a second arm member 312. In this example, these links are coupled via rotary joints, each rotary joint enabling the two linked members that are coupled by that rotary joint to rotate with respect to each other.

A support 306 can be used to support the arm 302 and, in some implementations, may be considered a proximal member of the arm 302. In some implementations, as shown, the support is mechanically grounded. In some examples, support 306 is provided in a user control system, such as a user control system 102 of FIG. 2. Support 306 can be connected to, or be part of, a frame or structure. For example, the support 306 can be rigidly coupled to a frame at one or more of its surfaces, e.g., a top surface, side surface, and/or other surface of the support 306.

A base motor 314 is rigidly coupled to the support 306. For example, base motor 314 includes a housing 316 that is rigidly coupled to the support 306. Base motor 314 includes a drive shaft (see FIG. 6) that extends along an axis 318 and is rotatable about the axis 318. In this example, the base motor housing 316 is rigidly coupled to a portion 317 of the support 306 that includes an aperture (not shown) through which the drive shaft of base motor 314 extends. Some examples of a motor that can be used as base motor 314 are described below with reference to FIGS. 8 and 9. Base motor 314 can be controlled via signals from a control circuit to output torque on and rotate its drive shaft about axis 318.

Base member 308 is rotatably coupled to support 306, e.g., at a proximal portion of base member 308, such that base member is rotatable about axis 318 with respect to support 306. In some implementations, base member 308 is rigidly coupled to the drive shaft of base motor 314 such that base motor 314 can exert torque upon and rotate base member 308 about axis 318 with respect to support 306. Thus, in these implementations, the drive shaft of base motor 314 is rotatable about the axis of rotation 318 of base member 308 with respect to the support 306.

In some implementations, the drive shaft of base motor 314 is directly coupled to base member 308 without use of a scaling mechanism (e.g., gear mechanism, capstan drive mechanism, etc.) that increases or decreases the torque output of base motor 314 on base member 308, e.g., no gearing or scaling of the motor output torque is performed. Thus, a 1:1 drive ratio (akin to 1:1 gear ratio) of output torque is provided from the output of base motor 314 to base member 308. This direct connection of shaft to base member and lack of output scaling allows low friction in the force (torque) transmission to the base member via the rotary bearings of base motor 314. This configuration avoids amplifying friction and or torque disturbances (ripple) in the base motor by a gear ratio as when using a scaling mechanism, and avoids introducing additional friction from the scaling mechanism to the torque transmission.

In some implementations, axis 318 extends vertically with respect to a user, e.g., extends orthogonally to a ground surface (e.g., floor) that supports the support 306 and/or other frame or structure that is connected to support 306. Other orientations of axis 318 can be used in other implementations. Rotation of base member 308 about axis 318 provides a rotary degree of freedom 319, e.g., control input device 304 can be rotated in rotary degree of freedom 309 via the arm 302.

In some implementations, one or more sensors can be coupled to the arm 302 to detect the rotation and/or orientation of base member 308 about axis 318 in the rotational degree of freedom 310. For example, the sensor can send signals describing the rotation and/or orientation to a control circuit, e.g., of the teleoperated system 100. In some implementations, the control circuit can provide control signals that are sent to a controlled device such as manipulator system 104 described above.

For example, a sensor 323 can be coupled to base motor 314 to detect rotation of the drive shaft of base motor 314 about axis 318. In some examples, sensor 323 is a rotary sensor such as a rotary encoder that senses the orientation of the drive shaft about axis 318, or can be a different type of sensor. Sensing the orientation of the drive shaft provides an orientation of base member 308 about axis 318 since the base member is rigidly coupled to the drive shaft. In some implementations, one or more other sensors can be additionally or alternatively used. For example, a secondary sensor 325 can be coupled to base motor 314 and additionally sense the rotation of the drive shaft of base motor 314, examples of which are described below with respect to FIG. 7.

A first arm motor 322 is rigidly coupled to base member 308. For example, first arm motor 322 includes a housing 324 that is rigidly coupled to base member 308. First arm motor 322 includes a drive shaft (see FIG. 6) that extends along and is rotatable about the axis 326. The drive shaft of first arm motor 322 is directly and rigidly coupled to first arm member 310. In this example, first arm motor housing 324 is rigidly coupled to a portion 328 of base member 308 that includes an aperture (not shown) through which the drive shaft of first arm motor 322 extends. Some examples of a motor that can be used as first arm motor 322 are described below with reference to FIGS. 8 and 9. First arm motor 322 can be controlled via signals from a control circuit to output torque on and rotate its drive shaft about axis 326.

In some implementations, a second arm motor 330 is also rigidly coupled to base member 308. For example, second arm motor 330 includes a housing 332 that is rigidly coupled to base member 308. Second arm motor 330 includes a drive shaft (see FIG. 6) that is rotated by the second arm motor 330 about axis 326. The drive shaft of second arm motor 330 is directly and rigidly coupled to a force transmission mechanism that is coupled to second arm member 312, e.g., a torque transmission mechanism in this example. For example, the drive shaft can be rigidly coupled to a first pulley as described below with respect to FIGS. 4 and 5. In this example, the second arm motor housing 332 is rigidly coupled to a portion 334 of base member 308 that includes an aperture (not shown) through which the drive shaft of second arm motor 330 extends. Some examples of a motor that can be used as second arm motor 330 are described below with reference to FIGS. 8 and 9. Second arm motor 330 can be controlled via signals from a control circuit to output torque on and rotate its drive shaft about axis 326.

First arm member 310 includes a first portion that is rotatably coupled to a second portion of base member 308 by a rotary coupling, such that first arm member 310 rotates about axis 326 with respect to base member 308 at the rotary coupling. For example, a proximal end of first arm member 310 is rotatably coupled to the drive shaft of motor 322. Rotation of first arm member 310 about axis 326 provides a rotary degree of freedom 327, e.g., the control input device 304 can be rotated in rotary degree of freedom 327 via the arm 302. In the described implementation, the first portion of first arm member 310 is rigidly coupled to the drive shaft of first arm motor 322 such that first arm motor 322 can exert torque upon and rotate first arm member 310 about axis 326 with respect to base member 308. Thus, the drive shaft of first arm motor 322 is rotatable about the axis of rotation (axis 326) of first arm member 310 with respect to base member 308. In the described implementation, the first portion of first arm member 310 is positioned between two portions 328 and 334 of base portion 334 and rotates between these portions.

The drive shaft of first arm motor 322 is directly coupled to first arm member 310 without use of a scaling transmission (e.g., gear mechanism, capstan drive mechanism, etc.) that increases or decreases the torque output of motor 322 on the first arm member 310, e.g., there is no gearing or scaling of the motor output torque. Thus, a 1:1 drive ratio of output torque is provided from the output of first arm motor 322 to first arm member 310. This direct connection of shaft to arm member and lack of output scaling allows low friction in the torque transmission to the first arm member via the rotary bearings of the first arm motor 322. This configuration avoids amplifying friction and or torque disturbances (ripple) in the first motor by a gear ratio as when using a scaling mechanism, and avoids introducing additional friction from the scaling mechanism.

Second arm member 312 includes a first portion that is rotatably coupled to a second portion of first arm member 310 by a rotary coupling. For example, a proximal end of second arm member 312 is rotatably coupled to a distal end of first arm member 310. Second arm member 312 can be rotated about an axis 336 with respect to first arm member 310 at the rotary coupling. In some implementations, as shown, axis 336 is parallel to axis 326. Rotation of second arm member 312 about axis 336 provides a rotary degree of freedom 337, e.g., control input device 304 can be rotated in rotary degree of freedom 337 via the arm 302. In some implementations, a torque transmission mechanism is provided between second arm motor 330 and second arm member 312 such that the second arm member 312 is driven by second arm motor 330 via the transmission mechanism. In some examples, the transmission mechanism can include a first pulley that is rigidly coupled to the drive shaft of second arm motor 330, a second pulley rigidly coupled to the second arm member 312, and a tension element connecting the first pulley to the second pulley. This allows second arm motor 322 to exert torque upon and rotate second arm member 312 about axis 336 with respect to first arm member 310 and base member 308. Examples of such an implementation are described in greater detail below with respect to FIGS. 4 and 5.

In some implementations, the drive shaft of second arm motor 330 is directly coupled to the torque transmission mechanism (e.g., to the first pulley) without use of a scaling mechanism (e.g., gear mechanism, capstan drive mechanism, etc.) that increases or decreases the torque output of the motor 330 on the second arm member 312, e.g., there is no gearing or scaling of the second arm motor output torque. Thus, a 1:1 drive ratio of output torque is provided from the output of second arm motor 330 to second arm member 312 (e.g., via a torque transmission mechanism as described below). This transmission of shaft torque to arm member and lack of output scaling allows low friction in the torque transmission to the second arm member via the rotary bearings of the second arm motor 330. This configuration avoids amplifying friction and or torque disturbances (ripple) in the second motor by a gear ratio as when using a scaling mechanism, and avoids introducing additional friction from the scaling mechanism.

In some implementations, the arm 302 is configured such that base motor 314, first arm motor 322, and second arm motor 330 are the identical type of motor, e.g., the same construction, parts, assembly, and implementation. In some implementations, first arm motor 322 and second arm motor 330 are the identical type of motor, e.g., the same construction, parts, assembly, and implementation. The use of the same motor type for motors 314, 322, and/or 330 allows easier and cheaper manufacturing and assembly for multiple parts of the arm assembly 300.

In the described implementation, first arm motor 322 and second arm motor 330 are positioned such that their drive shafts rotate about the same rotary axis 326. In some implementations, as shown in FIG. 3, motors 322 and 330 are positioned opposite to each other, e.g., on opposing sides of base member 308, such that first arm motor 322 is oriented in the opposite direction to second arm motor 330 along the rotational axis 326. The co-axial arrangement of the first arm motor 322 and second arm motor 330 allows the described torque transmission mechanism to properly transmit torque from the second arm motor 330 to the second arm member 312 without applying a torque on the first arm 310. For example, the first pulley (e.g., pulley 626 of FIG. 6) that is coupled to the drive shaft of the second arm motor 330 is positioned to rotate about the same axis about which first member arm 310 rotates. When the first member arm 310 rotates about axis 326, the tension member extending along the first arm member 310 also rotates about axis 326 (e.g., the first arm 310 and the first pulley rotate independently). Thus the coaxial arrangement of the first arm member, first and second arm motors, and pulley allows the tension element to remain tightly wrapped around the first pulley when the first member arm 310 rotates about axis 326. If, for example, the first pulley did not rotate about the same axis about which the first arm member 310 rotates, then the tension member may get tighter or looser as the first arm member rotates about axis 326, causing interference in torque transmission from the second arm motor to the second arm member. Other types of torque transmission mechanisms (e.g., rigid link, etc.) may similarly not operate properly when the first arm member is rotated, if the drive shaft of the second arm motor is not aligned with axis 326.

In some implementations, the first arm motor 322 and second arm motor 330 can be positioned on or close to first arm member 310 to provide a compact configuration that reduces inertia about axis 318 when rotating the arm 302. In some implementations, the direct coupling of the motors to the driven members allows for a much smaller package for the arm assembly 300, e.g., by compacting the volume of area needed for the motors and arm components. The compact configuration of motors can also benefit user operation of the arm assembly by reducing blockage of views or sight lines of the operating user. Furthermore, a co-axial arrangement of first arm motor 322 and second arm motor 330, as described above for some implementations, allows a compact configuration of the two motors with first arm member and results in similar benefits described above. Some implementations that position base motor 314 close to the axis 326 of first arm motor 322 and second arm motor 330, as shown in FIG. 3, provides a compact configuration occupied by base motor 314, first arm motor 322, and second arm motor 330 and results in similar benefits described above.

In some implementations, second arm motor 330 can be positioned in other locations of the arm assembly 300 such that its drive shaft is not aligned with rotary axis 326. For example, the drive shaft of second arm motor 330 can be aligned with the axis 336, allowing the second drive shaft to be directly and rigidly coupled to second arm member 312 without use of a torque transmission mechanism. In some implementations, second arm motor 330 is not used in arm assembly 300, e.g., second arm member 312 is not driven by a motor or other active actuator. In some implementations, base motor 314 is not used in arm assembly 300, e.g., base member 308 is not driven by a motor or other active actuator. In some implementations, first motor 322 is not used in arm assembly 300.

In various implementations, base member 308 can be provided as a third arm member, e.g., can be rotatably coupled to the support 306 about an axis parallel to axis 326 and 336 instead of, or in addition to, being rotatable about axis 318. In some of these implementations, a motor can apply torque to the base member about that parallel axis and have a drive shaft rotatable about that parallel axis. In some implementations, base member 308 can be extended to greater length than shown in FIG. 3, e.g., similar to the lengths of first arm member 310 and/or second arm member 312.

In some implementations, one or more sensors can be coupled to the arm 302 to detect the rotation and/or orientation of the first arm member 310 about axis 326 in the rotational degree of freedom 327. For example, the sensor can send signals describing the rotation and/or orientation of first arm member 310 to a control circuit, e.g., of the teleoperated system 100. In some implementations, the control circuit can provide control signals that are sent to manipulator system 104 as described above.

For example, a sensor 340 can be coupled to the first arm motor 322 to detect rotation of the drive shaft of the first arm motor 322 about axis 326. In some examples, sensor 340 is a rotary sensor such as a rotary encoder that senses the orientation of the drive shaft about axis 326, or can be a different type of sensor. Sensing the orientation of the drive shaft provides an orientation of first arm member 310 about axis 326 since the first arm member 310 is rigidly coupled to the drive shaft. In some implementations, one or more other sensors can be additionally or alternatively used. For example, a secondary sensor 342 can be coupled to the first arm motor 322 and additionally sense the rotation of the drive shaft of the first arm motor 322, as described below with respect to FIG. 7.

In some implementations, one or more sensors can be coupled to the arm 302 to detect the rotation and/or orientation of second arm member 312 about axis 336 in the rotational degree of freedom 337. For example, the sensor can send signals describing the rotation and/or orientation of second arm member 312 to a control circuit, e.g., of the teleoperated system 100. In some implementations, the control circuit can provide control signals that are sent to manipulator system 104 as described above.

For example, a sensor 346 (see FIG. 4) can be coupled to the second arm motor 330 to detect rotation of the drive shaft of the second arm motor 330 about axis 326. In some examples, sensor 346 is a rotary sensor such as a rotary encoder that senses the orientation of the drive shaft about axis 326, or can be a different type of sensor. Sensing the orientation of the drive shaft provides an orientation of second arm member 312 about axis 336 since the second arm member 312 is coupled to the drive shaft via a torque transmission mechanism (e.g., pulleys and tension member as described with reference to FIGS. 4 and 5). In some implementations, one or more other sensors can be additionally or alternatively used. For example, a secondary sensor (see FIG. 4) can be coupled to the second arm motor 330 and additionally sense the rotation of the drive shaft of the second arm motor 330 as described below.

In some implementations, one or more gravity compensation mechanisms (e.g., counterbalance mechanisms) are coupled to arm 302 to exert torques, for example, on first arm member 310 and second arm member 312 in opposition to the force of gravity. For example, a first compensation mechanism 350 can be used to apply compensation torque to first arm member 310 and a second compensation mechanism 351 can be used to apply compensation torque to second arm member 312. Example gravity compensation mechanisms are described in greater detail with respect to FIG. 7. In some implementations, one or more of first arm motor 322 and second arm motor 330 (and/or base motor 314 if its axis of rotation is oriented non-vertically) can be used additionally or alternatively to the gravity compensation mechanisms to output gravity compensation torques on the arm 302.

Control input device 304 is coupled to a second (distal) portion of second arm member 312. In some implementations, control input device 304 is rotatably coupled to second arm member 312. In other implementations, control input device 304 can be coupled in other ways, e.g., rigidly coupled or translatably coupled to second arm member 312.

Control input device 304 shown in FIG. 3 is one example of an input device that can be coupled to a distal end of the arm 302. In this example, control input device 304 includes a handle 350 that is grasped by a user, e.g., by fingers and/or palm of a hand of the user. Some examples of a control input device are described below with respect to FIG. 10. Arm 302 provides multiple degrees of freedom to handle 350 based on the rotary joints of the arm described above, e.g., rotation of links of the arm 302 about axes 318, 326, and 336.

In some implementations, as in the example shown in FIG. 3, control input device 304 provides degrees of freedom to handle 350 which are in addition to the degrees of freedom provided to handle 350 by the arm 302. For example, a gimbal mechanism 304 or other linkage can couple handle 350 to a distal portion of second arm member 312, where each link is rotatably coupled to one or more other links in the gimbal mechanism. Further examples of gimbal mechanism 304 are described below with respect to FIG. 10.

Figure 4:
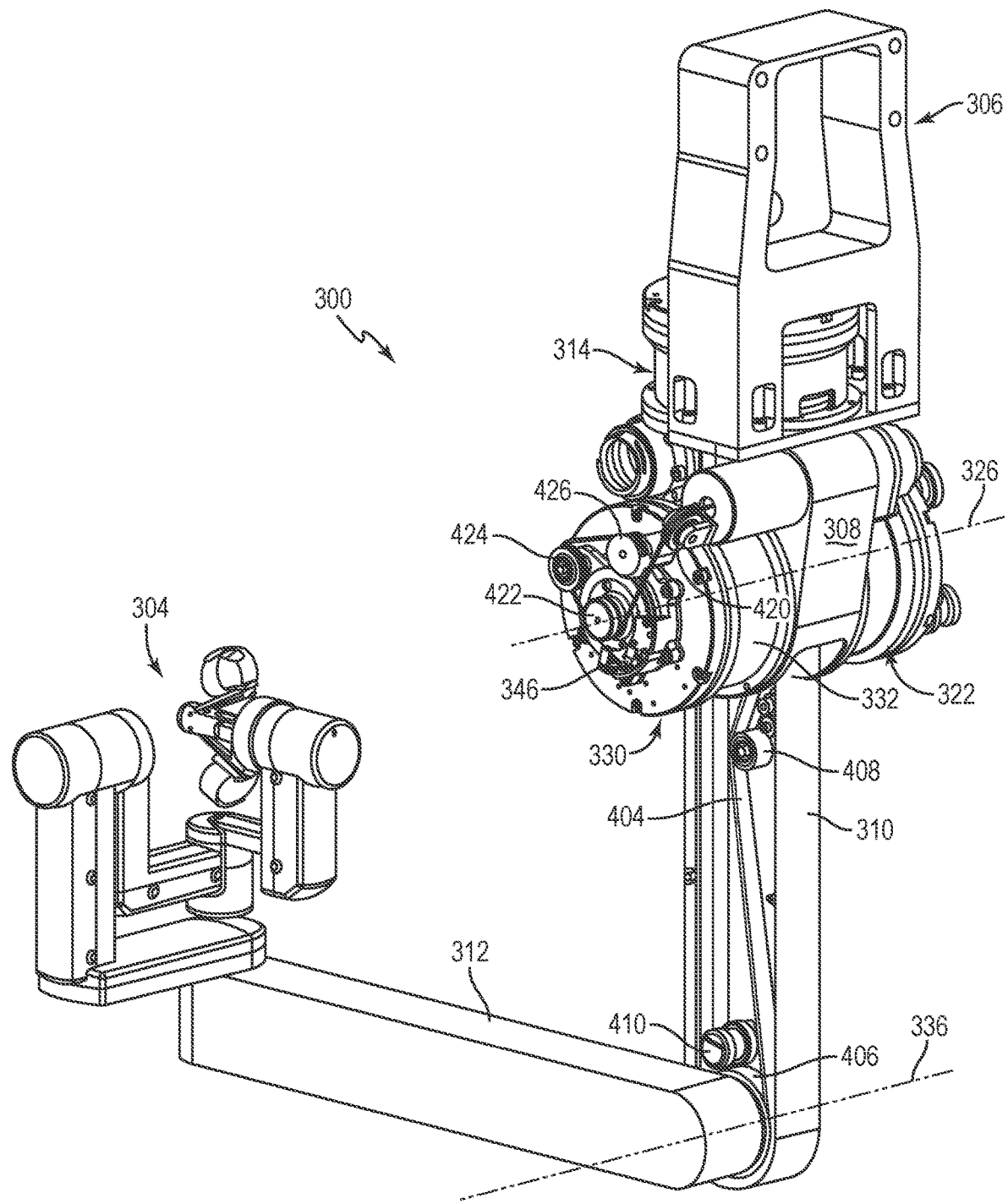
FIG. 4 is a second perspective view of the arm assembly of FIG. 3, according to some implementations.
Figure 5:
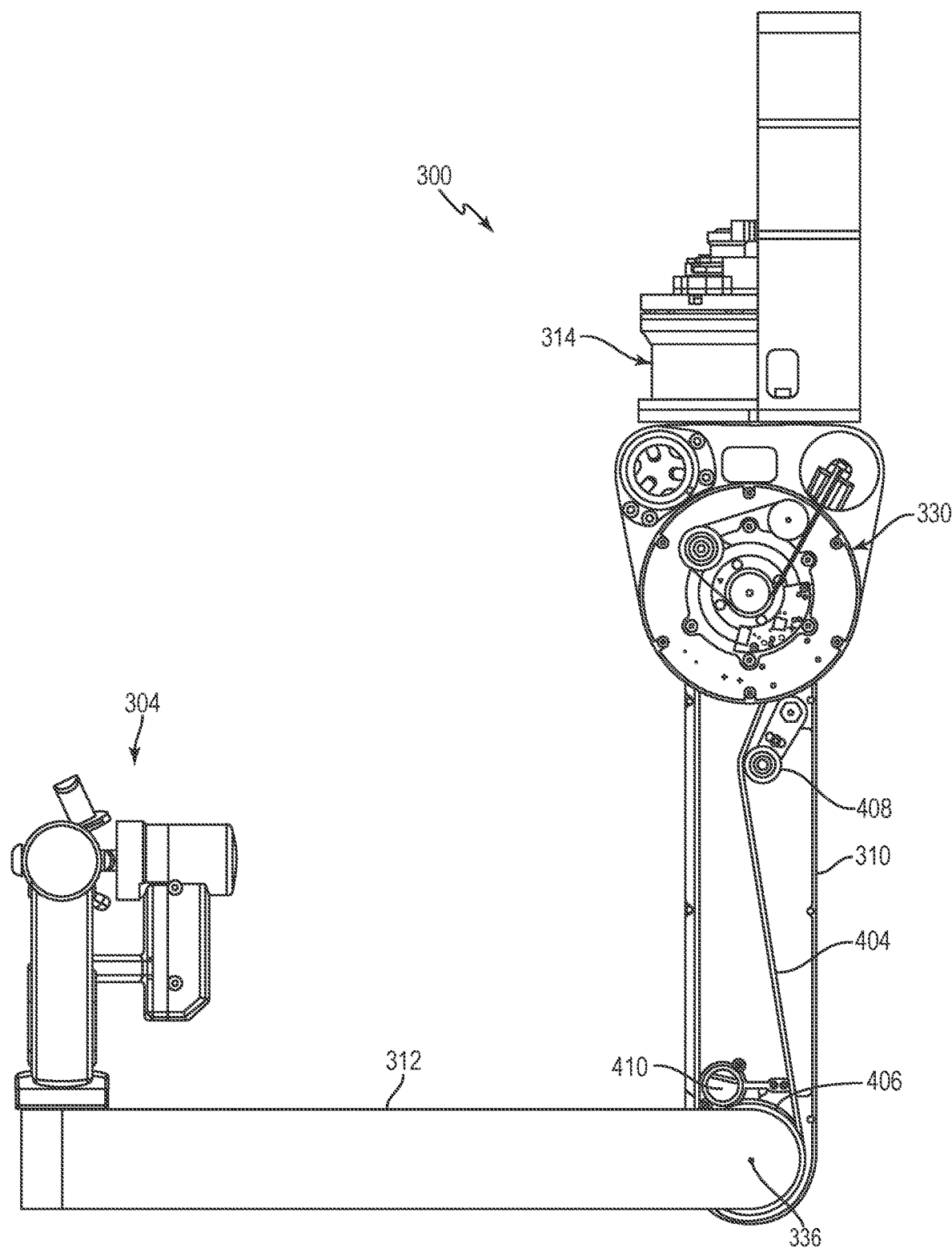
FIG. 5 is a side elevational view of the arm assembly of FIG. 3, according to some implementations.

FIG. 4 is a perspective view of the arm 302 of FIG. 3. Arm 302 is shown with a portion of the interior of first arm member 310 exposed. FIG. 5 is a side elevational view of the arm 302 of FIG. 3, with a similar portion of the interior of first arm member 310 exposed.

In this example, a pulley transmission mechanism is provided in first arm member 310 as a torque transmission mechanism coupling the second arm motor 330 to the second arm member 312. As shown, first arm member 310 includes a tension element that is a belt 404 coupled to (wrapped around) a first pulley (see FIG. 6) that is positioned within the proximal portion of first arm member 310, and the first pulley is rigidly coupled to the drive shaft of second arm motor 330. For example, belt 404 can be made of stainless steel or other material of suitable strength, or can be a cable, rope, chain, or other type of tension element. Belt 404 extends along the length and in the interior of first arm member 310 to the distal portion of first arm member 310, where belt 404 is wrapped around a second pulley 406. Second pulley 406 is rotatably coupled to the distal portion of first arm member 310 and is rigidly coupled to the proximal portion of second arm member 312. Second pulley 406 is caused to rotate about axis 336 by movement of belt 404.

In some implementations, belt 404 can be at least partially wrapped around one or more rollers to provide tension on belt 404. For example, belt 404 is partially wrapped around roller 408 that is rotatably coupled to first arm member 310. In some implementations, roller 408 can be coupled to a spring-tensioned member to provide spring force against belt 404.

The torque transmission mechanism, including the first pulley 626, belt 404, and second pulley 406, transmits rotational torques from second arm motor 330 to second arm member 312. For example, second arm motor 330 is controlled to rotate the first pulley, which causes belt 404 to move and causes second pulley 406 to rotate. The rotation of second pulley 406 exerts torque on, and/or causes rotation of, second arm member 312 about axis 336.

In other implementations, a different type of torque transmission mechanism can be used instead of the pulley transmission mechanism shown in FIGS. 4 and 5. For example, a rigid member can be rotatably coupled to the first pulley (or a driven plate similar to a pulley), or can be rotatably coupled to the drive shaft or other rotating portion of the second arm motor, at a location offset from axis 326. The rigid member extends parallel to first arm member 310 and is rotatably coupled to the second arm member 312 at a location offset from axis 336. In some examples, the rigid member, first arm member 310, and lines drawn between the rotary couplings of the rigid member and first arm member 310 can form a parallelogram. As the first pulley rotates, the rigid member is moved away from and toward the first pulley, which moves the second arm member 312 about axis 336 with respect to first arm member 310 in corresponding directions.

Sensor 346 is coupled to second arm motor 330 to sense the orientation of the drive shaft of the motor and thereby sense the position of the second arm member 312 as described above. In some implementations, a secondary sensor 410 can be used to sense the rotation of second pulley 406 and thus sense the rotation of second arm member 312 about axis 336, e.g., as redundant sensing to sensor 346. For example, secondary sensor 410 can be a rotary encoder or other type of sensor that is coupled to a gear (not shown) that engages a toothed edge of second pulley 406. The gear of the sensor rotates in conjunction with second pulley 406 (e.g., the sensor gear engages with a sector gear mounted to pulley 406), allowing the secondary sensor 410 to sense the rotation of the second pulley 406. Other types of sensors can also or alternatively be used.

Also shown are pulley 420, pulley 422, pulley 424, and post 426, which are used in a counterbalancing mechanism as described below with respect to FIG. 7.

Figure 6:
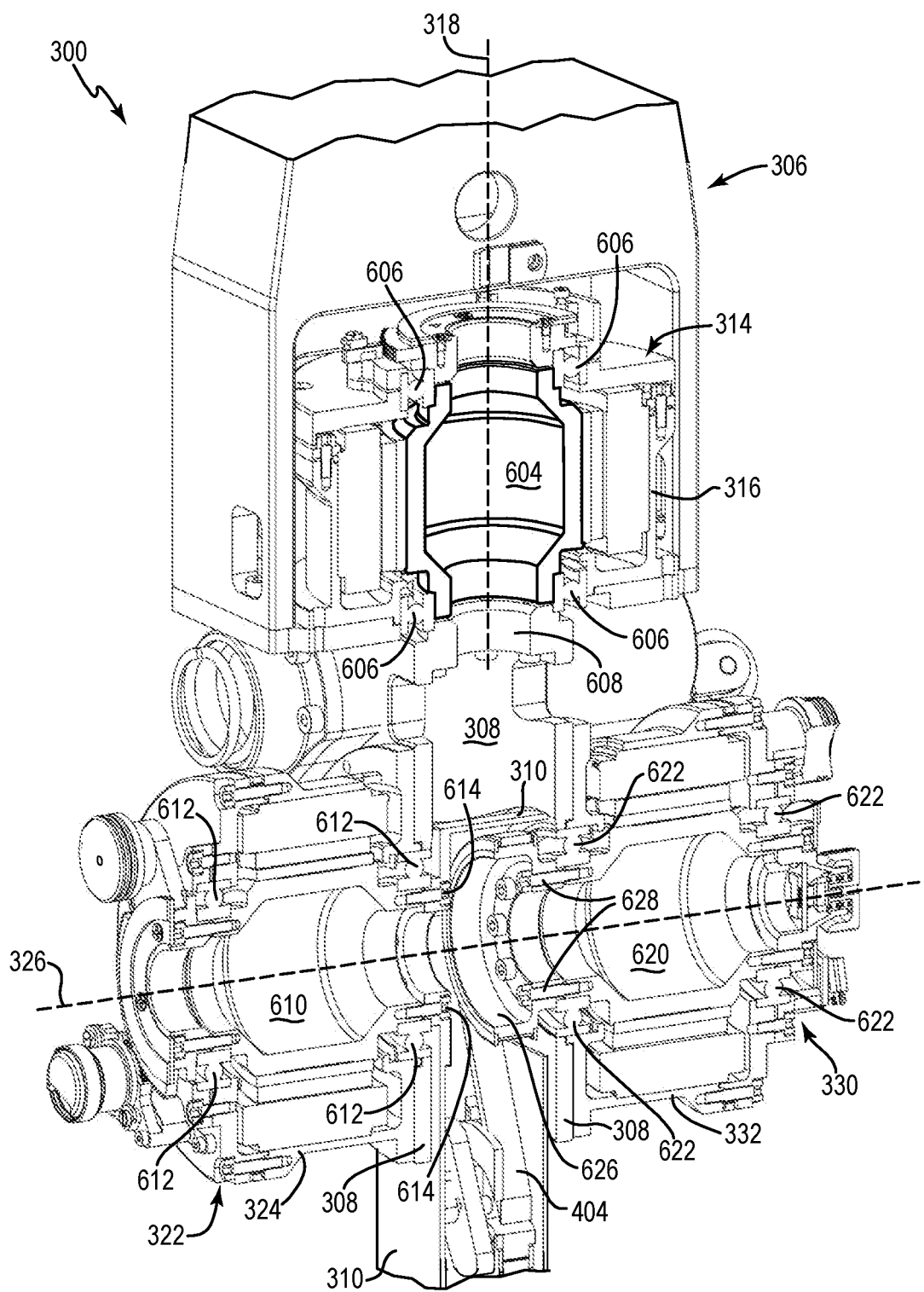
FIG. 6 is a perspective view of a cutaway portion of the arm assembly of FIG. 3, according to some implementations.

FIG. 6 is a perspective view of a cutaway portion of the arm assembly 300 of FIG. 3 including support 306, base member 308, and a portion of first arm member 310. The interiors of these components of the arm assembly 300, and example interiors of base motor 316, first arm motor 322, and second arm motor 330 are shown.

Base motor 314 rotates a drive shaft 604 that is coupled to rotary bearings 606. Bearings 606 permit the drive shaft 604 to rotate with respect to the housing 316, stator, and other components of the base motor 316 (e.g., see below with respect to FIG. 9). Drive shaft 604 is rigidly coupled to a portion 608 of base member 308 such that the drive shaft 604 applies torque to, and may rotate, base member 308 with respect to support 306.

First arm motor 322 rotates a drive shaft 610 that is coupled to rotary bearings 612. Bearings 612 permit the drive shaft 610 to rotate about axis 326 with respect to the housing 324, stator, and other components of the first arm motor 316 (e.g., see below with respect to FIG. 9). Drive shaft 610 is rigidly coupled to first arm member 310, e.g., by fasteners 614 such as screws, rivets, etc. Drive shaft 610 applies torque to, and may rotate, first arm member 310 with respect to base member 308.

Second arm motor 330 rotates a drive shaft 620 that is coupled to rotary bearings 622. Bearings 622 permit the drive shaft 620 to rotate with respect to the housing 332, stator, and other components of the second arm motor 330 (e.g., see below with respect to FIG. 9). Drive shaft 620 is rigidly coupled to first pulley 626, e.g., by fasteners 628 such as screws, rivets, etc. Drive shaft 620 applies torque to, and may rotate, first pulley 626 about axis 326 with respect to base member 308 and first arm member 310. First pulley 626 can be coupled to belt 404 as described above. In this example, belt 404 is coupled to a second pulley 406 and second arm member 312 as shown in FIG. 4.

Figure 7:
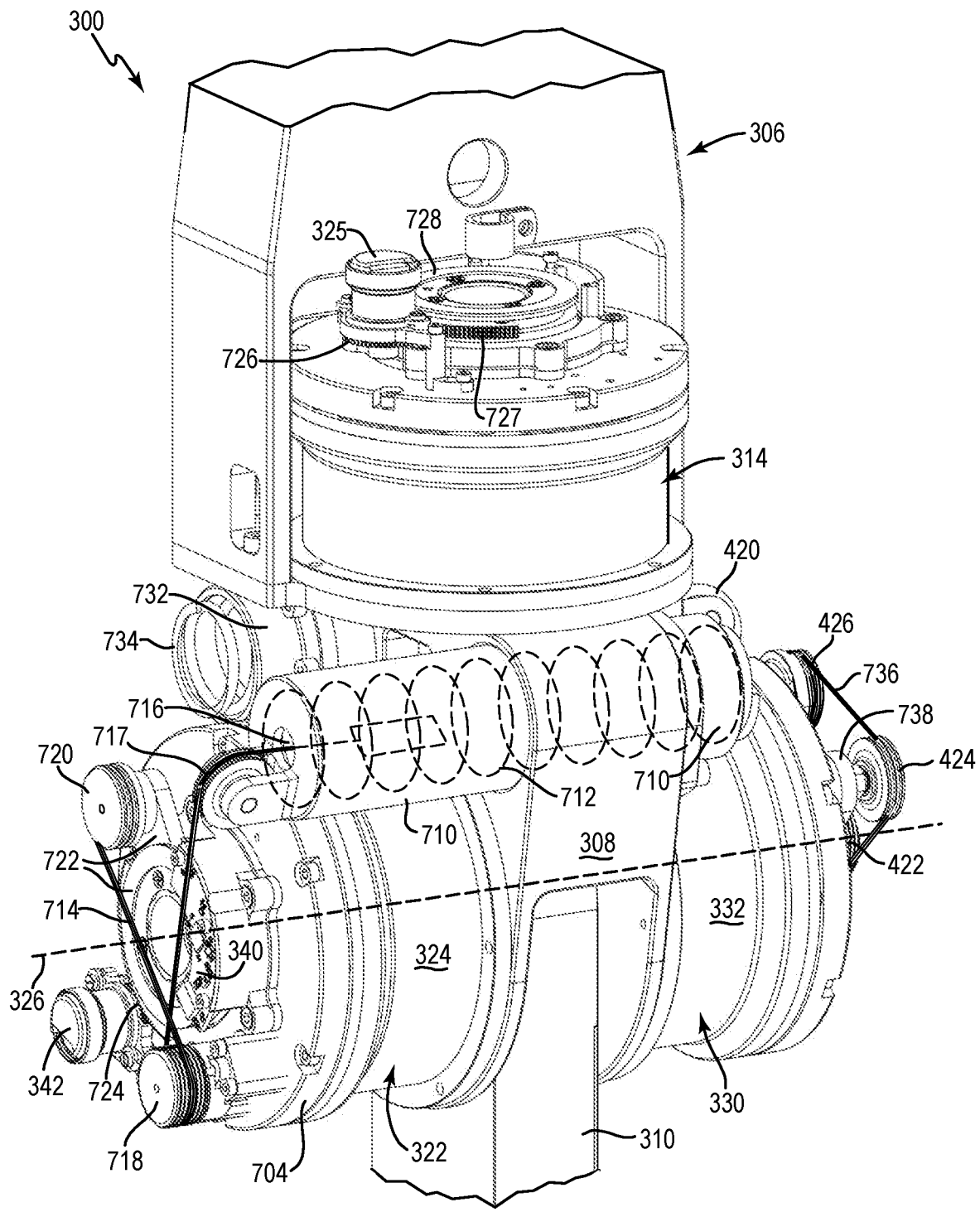
FIG. 7 is a perspective view of the portion of the arm assembly of FIG. 6, according to some implementations.

FIG. 7 is a perspective view of the portion of the arm assembly 300 of FIG. 6, including support 306, base member 308, and a portion of first arm member 310.

In some implementations, a counterbalancing mechanism is included to provide torques opposing gravitational forces on the arm members of arm assembly 300, e.g., allowing motor output to be reduced and easing manipulation of the coupled control input device 304 for a user. In some implementations, the counterbalancing mechanism includes a spring housing 710 that houses a spring 712, where the housing 710 and one end of spring 712 are coupled to the base member 308. A cable 714 is coupled to the spring 712 and is routed out of an opening 716 of the spring housing 710 and around a pulley 717 coupled to the spring housing 710. Cable 714 can be a single cable that is doubled as shown in FIG. 7, can be two cables, or can be a single non-doubled cable in various implementations. Cable 714 is further routed around a pulley 718 (e.g., cylinder) that is rotatably coupled to the housing 324 of first arm motor 322. The cable is terminated at a post 720 that is rigidly coupled to a rotating portion 722 of the first arm motor 322 that is rigidly coupled to the rotating drive shaft 610 of first arm motor 322. Rotating portion 722 rotates with the rotation of drive shaft 610 and first arm member 310.

The counterbalancing mechanism provides counterbalancing torques on the rotation of first arm member 310 about axis 326. For example, as first arm member 310 rotates in either direction about axis 326, the rotating portion 722 rotates, which causes the cable 714 to pull on the spring 712. The spring 712 resists this pull, providing a counterbalancing torque to the rotation of the first arm member 310 about axis 326. Other types or configurations of counterbalancing mechanisms can be used in other implementations.

In some implementations, a similar counterbalancing mechanism is provided for second arm motor 330, as shown in FIGS. 4 and 7. The counterbalancing mechanism includes a spring housing 732 that houses a spring 734 coupled to the base member 308. A cable 736 is coupled to the spring 734 and is routed out of an opening (shown in FIG. 4) of the spring housing 732 and around a pulley 420 coupled to the spring housing 732. In some examples, cable 736 can be a single cable that is doubled, or can be two cables. The cable 736 is further routed around a pulley 422 that is rotatably coupled to the second arm motor 330. The cable 736 is then routed around a pulley 424 that is rotatably coupled to a rotating portion 738 that is rigidly coupled to the rotating drive shaft 620 of second arm motor 332. Rotating portion 738 rotates with the rotation of drive shaft 620 and first pulley 626. Rotating portion 738 thus rotates with second arm member 312 that is connected to the first pulley 626 via the second pulley 406 and belt 404. The cable 736 is then terminated at a post 426 (e.g., cylinder) that is rigidly coupled to the motor housing 332.

The cable 736 and spring 734 provide counterbalancing torques on the rotation of second arm member 312 about axis 336. For example, as second arm member 312 rotates in either direction about axis 336, the rotating portion 738 rotates, which causes the cable 736 to pull on the spring 734. The spring 734 resists this pull, providing a counterbalancing torque to the rotation of the second arm member 312 about axis 336. Other types or configurations of counterbalancing mechanisms can be used in other implementations.

Secondary sensor 342 can be, for example, a rotary encoder or other type of sensor, and is coupled to a rotating gear 724 that engages a sector gear coupled to the rotating portion 722. The rotation of rotating portion 722, coinciding with the rotation of the drive shaft of the first arm motor 322, is sensed by secondary sensor 342 via the rotating gear 724. Similarly, secondary sensor 325 (e.g., a rotary encoder or other type of sensor) is coupled to a rotating gear 726 that engages a sector gear 727 coupled to the rotating portion 728 of base motor 314. Rotating portion 728 is rigidly coupled to the drive shaft of base motor 314, such that rotation of the drive shaft is sensed by secondary sensor 325 via the rotating gear 726.

Figure 8:
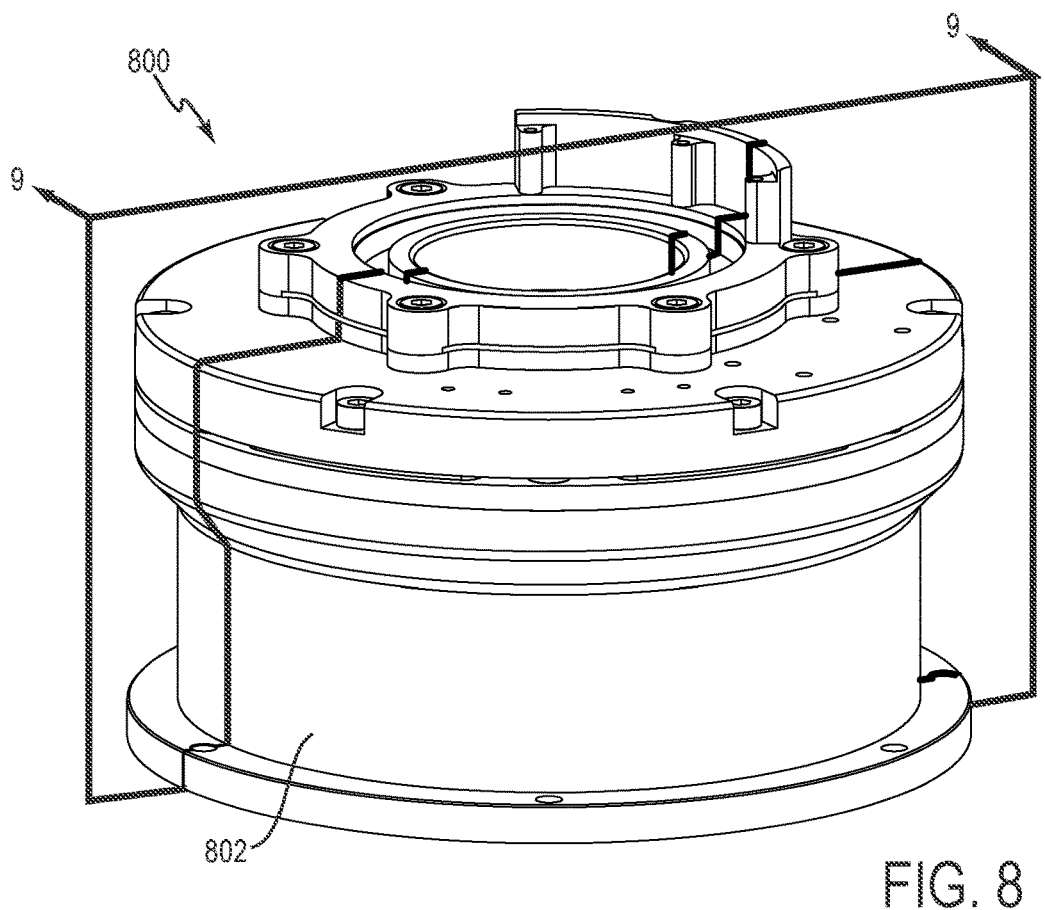
FIG. 8 is a diagrammatic illustration of an example motor which can be used as one or more of the motors of the arm assembly, according to some implementations.

FIG. 8 is a perspective view of an example motor 800 which can be used as one or more of the motors of the arm assembly implementations described herein. For example, motor 800 can be used as base motor 314, first arm motor 322, and/or second arm motor 330 in arm assembly 300 of FIG. 3. In this example, motor 800 includes a housing 802.

Figure 9:
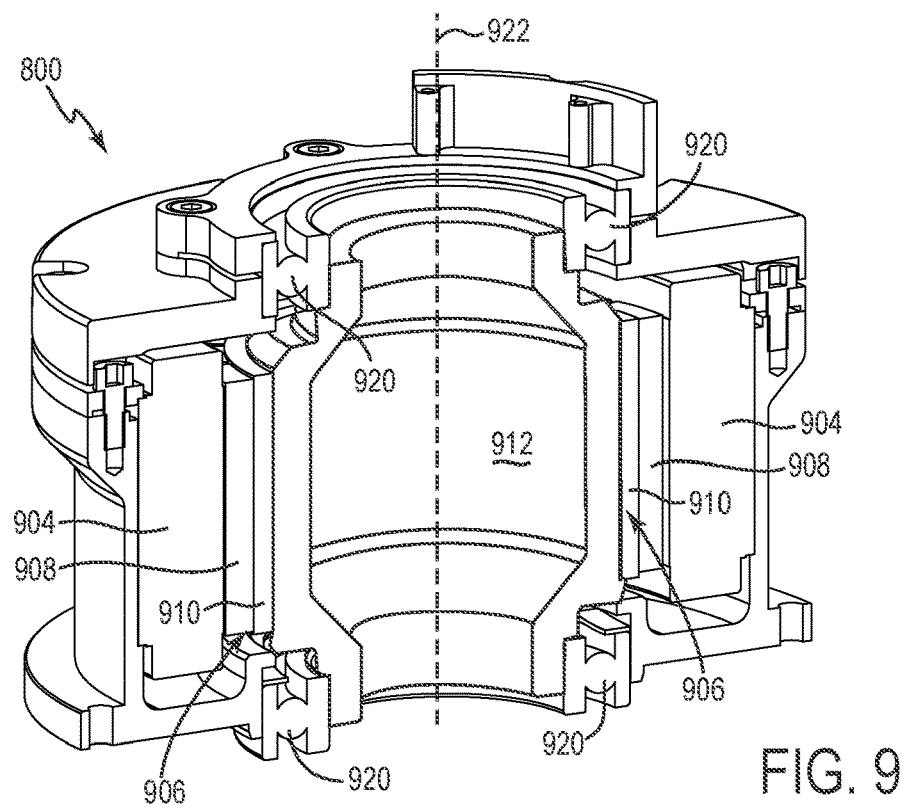
FIG. 9 is a sectional perspective view of the motor of FIG. 8, according to some implementations.

FIG. 9 is a sectional perspective view of the motor 800 along section plane 9-9 in FIG. 8. Motor 800 includes a stator 904. Stator 904 includes one or more windings or coils of electrical wire that provide a magnetic field based on electrical current induced in the wire.

Motor 800 also includes a rotor 906. Rotor 906 includes magnet layer 908 positioned adjacent to and within the inner circumference of the stator 904. Rotor 906 also includes a layer 910 coupled to magnet layer 908 and positioned within the inner surface of magnet layer 908. Core layer 910 can be made of ferromagnetic material and is the yolk/core of the rotor 906. Rotor 906 also includes a drive shaft 912 coupled (e.g., bonded) to core layer 910 and positioned within the inner surface of layer 910. For example, drive shaft 912 can be made of aluminum or other non-ferromagnetic material. The ferromagnetic material of core layer 910 completes the magnetic flux circuit. This allows shaft 912 to be aluminum or other material lighter than the core layer 910 for reduced inertia of the rotor 906. A top portion (not shown) can be rigidly coupled to the drive shaft 912 to provide a rotating portion similar to rotating portions 722 and 738 of motors 322 and 330, respectively, as described above with respect to FIG. 7.

Drive shaft 912 of rotor 906 is shown as hollow, and core layer 910 includes sufficient ferromagnetic material to allow a magnetic circuit to be completed. This hollow feature can reduce inertia of the motor 800 when it is moved through space attached to an arm assembly. Other implementations can provide material within the hollowed out portion of the drive shaft 912.

Rotor 906 is coupled to a rotary coupling that includes bearings 920, which bear the weight of the rotor 906 and allow the rotor 906 to rotate with respect to the stator 904 with low friction. Motor 800 is operative to rotate rotor 906 about axis 922 based on the electrical current provided in the wire of stator 904.

In some implementations, motor 800 is a brushless DC motor. Furthermore, motor 800 can be a slotless brushless motor to avoid cogging torque which reduces the fidelity of the feel of torques applied to the arm assembly and control input device contacted by a user.

In some implementations, motor 800 can be a brushed DC motor, which does not have cogging torque but may have a brush life limitation. In some implementations, motor 800 can be a slotted brushless motor. In some implementations, other types of motors can be used for one or more of the motors of the arm assembly.

Figure 10:
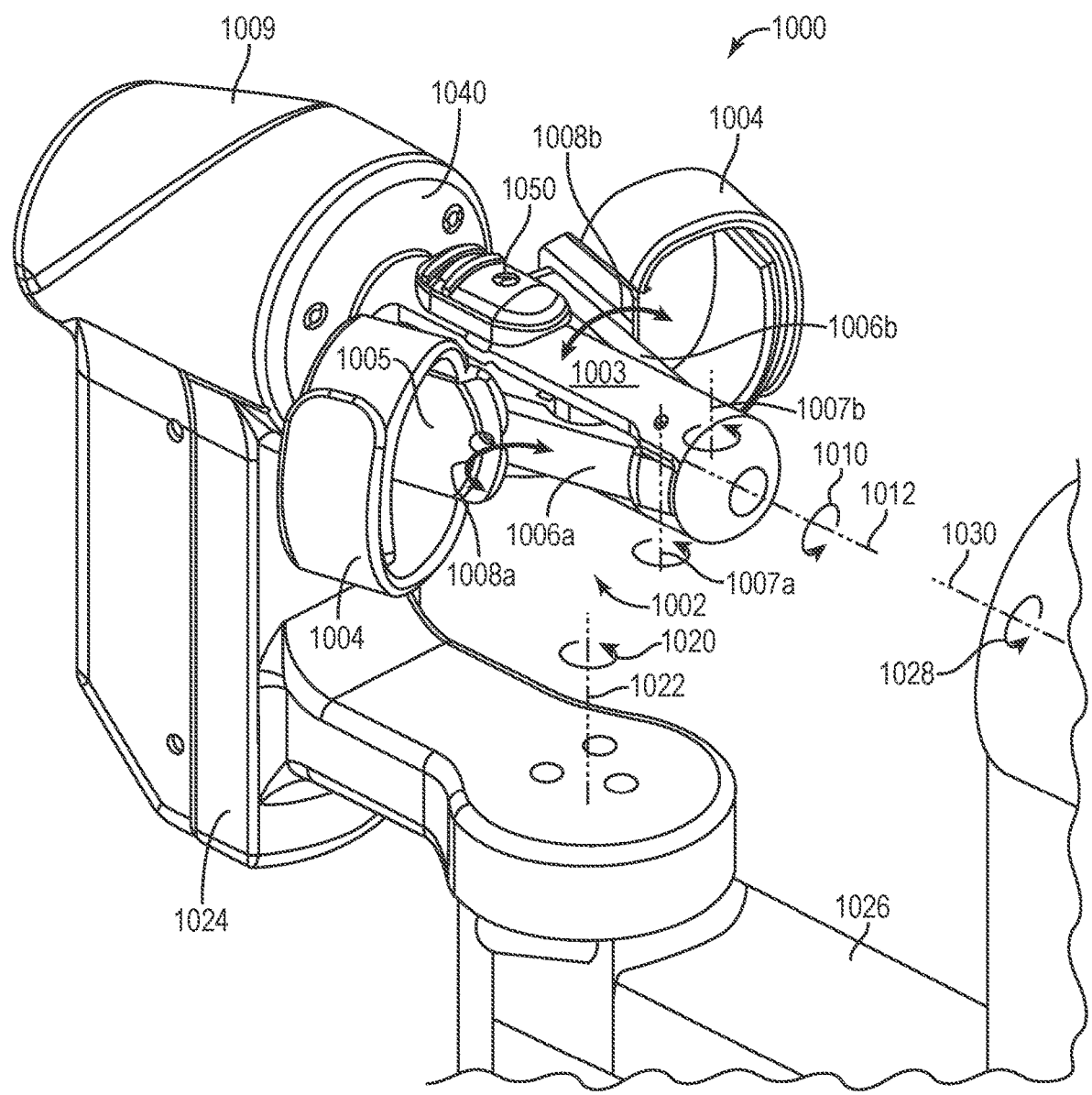
FIG. 10 is a perspective view of an example controller portion of a control input device, according to some implementations.

FIG. 10 is a perspective view of an example controller portion 1000 of a control input device which can be used in one or more implementations described herein. Controller portion 1000 can be used with any of the arm assembly implementations described herein. For example, controller portion 1000 can be a portion of control input device 304 as described with reference to FIG. 3, and/or can be included in a control input device 210 or 212 as described above with reference to FIGS. 1 and 2.

In some implementations, controller portion 1000 can be a mechanically grounded controller. For example, the controller portion 1000 can be coupled to a mechanical linkage such as the arm 302 of FIG. 3, that is coupled to ground or an object or support connected to ground, providing a stable platform for the use of the controller portion 1000.

Controller portion 1000 includes a handle 1002 which is contacted by a user to manipulate the control input device. In this example, the handle 1002 includes two grips that each include a finger loop 1004 and a grip member 1006 (grip members 1006a and 1006b). The two grip members 1006 are positioned on opposite sides of a central portion 1003 of the handle 1002, and the grip members 1006 can be grasped, held, or otherwise contacted by a user's fingers. In this example, finger contacts 1005 can be connected or formed at the unconnected end of the grip members 1006a and 1006b to provide surfaces to contact the user's fingers.

Each grip member 1006 and finger loop 1004 can be moved in an associated degree of freedom 1008 (e.g., 1008a and 1008b). In some examples, the grip members 1006a and 1006b are each coupled to the central portion 1003 of the handle 1002 at respective rotational couplings, allowing rotational movement of the grip members about grip axes 1007a and 1007b, respectively, with respect to the central portion 1003. Each grip member 1006a and 1006b can be moved in an associated degree of freedom 1008a about axis 1007a and degree of freedom 1008b about axis 1007b, respectively, e.g., by a user contacting the grip members. For example, in some implementations the grip members 1006a and 1006b can be moved simultaneously in a pincher-type of movement (e.g., toward or away from each other). In various implementations, a single grip member 1006 and finger loop 1004 can be provided, or only one of the grip members 1006 can be moved in the degree of freedom 1008 while the other grip member 1006 can be fixed with reference to the handle 1002. For example, the orientations of grip members 1006a and 1006b in their degrees of freedom can control corresponding rotational orientations of an end effector or other manipulator device instrument.

One or more grip sensors (not shown) can be coupled to the handle 1002 and/or other components of the controller portion 1000 and can detect the orientations of the grip members 1006a and 1006b in their degrees of freedom 1008. The sensors can send signals describing sensed orientations and/or motions to a control circuit, e.g., of the teleoperated system 100. In some modes or implementations, the control circuit can provide control signals to a manipulator device, e.g., manipulator system 104. For example, the orientations of the grip members 1006a and 1006b in degrees of freedom 1008a and 1008b can be used to control any of various degrees of freedom of an end effector of the manipulator system 104. Various implementations of the controller 1000 can provide one or more active actuators (e.g., motors, voice coils, etc.), passive actuators (e.g., brakes) or springs to output forces on the grip members 1006 in the degrees of freedom 1008.

Handle 1002 is also provided with a rotational degree of freedom 1010 about a roll axis 1012 defined between a first end and second end of the handle 1002. The roll axis 1012 is a longitudinal axis in this example that extends approximately along the center of the central portion 1003 of handle 1002. Handle 1002 can be rotated about axis 1012 with respect to a base member of the controller portion 1000, such as housing 1009. For example, a user can rotate the grip members 1006 and central portion 1003 as a single unit around the axis 1012, with respect to housing 1009, to provide control of a manipulator device, such as an end effector or other element of the manipulator system 104.

One or more sensors (not shown) can be coupled to the handle 1002 to detect the rotation and/or orientation of the handle 1002 in the rotational degree of freedom 1010. For example, the sensor can send signals describing the orientation to control circuits of the teleoperated system 100 which can provide control signals to the manipulator system 104 similarly as described above. For example, rotation of handle 1002 in degree of freedom 1010 can control a particular degree of freedom of an end effector of the manipulator device that is different than a manipulator degree of freedom controlled by degree of freedom 1008 of the grip members 1006.

In various implementations, the handle 1002 can be provided with additional degrees of freedom. In some implementations, the controller portion 1000 includes one or more gimbal mechanisms allowing multiple rotary degrees of freedom. For example, a rotational degree of freedom 1020 about a yaw axis 1022 can be provided to the handle 1002 at a rotational coupling between an elbow shaped link 1024 and a link 1026, and the elbow shaped link 1024 is coupled to the handle 1002 (e.g., at housing 1009). In this example, yaw axis 1022 intersects and is orthogonal to the roll axis 1012. For example, yaw axis 1022 can be similar to axis 232 shown in FIG. 2. Additional degrees of freedom can similarly be provided. For example, link 1026 can be elbow-shaped and a rotational coupling can be provided between the other end of link 1026 and another link (not shown in FIG. 10). A rotational degree of freedom 1028 about an axis 1030 can be provided to the handle 1002 at the rotational coupling. For example, axis 1030 can be similar to axis 230 shown in FIG. 2. In some examples, the controller portion 1000 and/or arm assembly 300 of FIG. 3 can allow movement of the handle 1002 within the workspace 114 of the user control system 102 with a plurality of degrees of freedom, e.g., six degrees of freedom including three rotational degrees of freedom and three translational degrees of freedom. One or more additional degrees of freedom can be sensed and/or actuated similarly as described above for the degrees of freedom 1008 and 1010. In some implementations, each additional degree of freedom of the handle 1002 can control a different manipulator degree of freedom (or other motion) of an end effector of the manipulator system 104. Various degrees of freedom can control other functions, e.g., of a manipulator device.

In an example implementation, handle 1002 is mechanically grounded, i.e., supported in space by a kinematic chain with an end stationary at mechanical ground, such as a floor, wall, or ceiling. For example, the housing 1009 can be coupled to a mechanical linkage that is coupled to the ground or an object connected to ground, providing a stable platform for the use of the hand controller portion 1000. In some implementations, the grounded mechanical linkage can be a linkage as described above with reference to FIG. 3.

Various kinematic chains, linkages, gimbal mechanisms, flexible structures, or combinations of two or more of these can be used with the controller portion 1000 in various implementations to provide one or more degrees of freedom to the controller portion. Some further examples of linkages and/or gimbal mechanisms that can be used with controller portion 1000 are described in U.S. Pat. No. 6,714,839 B2, which is incorporated herein by reference.

In the described example, handle 1002 includes one or more control switches 1050 or other type of input control, e.g., coupled to the central portion 1003 or to mechanisms within central portion 1003. In some implementations, the control switch 1050 can be moved to various positions to provide particular command signals, e.g., to select functions, options, or modes of the control console and/or control input device (e.g., a controlling mode or non-controlling mode as described herein), to command a manipulator system, other manipulator device, or other system in communication with the control input device, etc.

Figure 11:
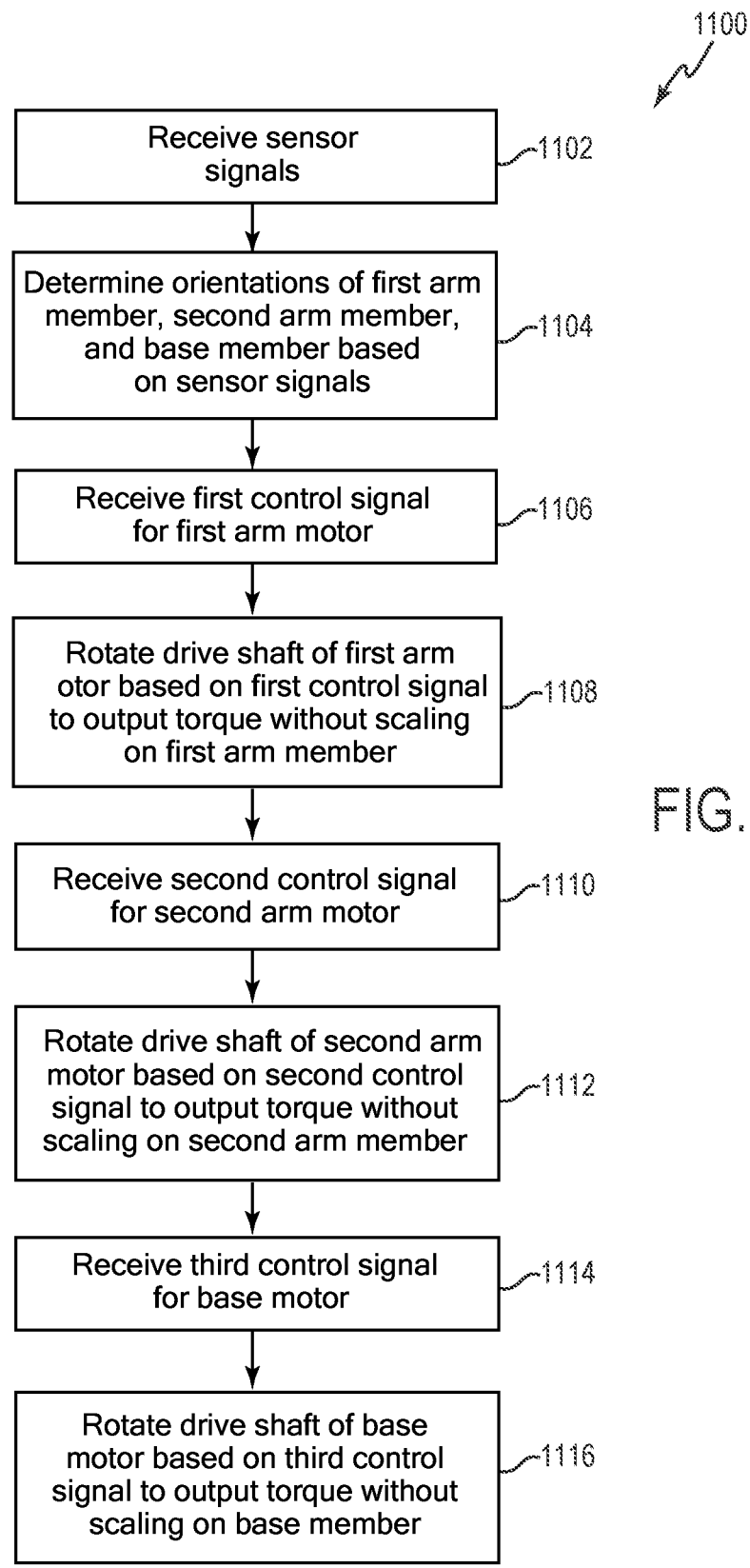
FIG. 11 is a flow diagram illustrating an example method to control motors of an arm, according to some implementations.

FIG. 11 is a flow diagram illustrating an example method 1100 to control motors of an arm, according to some implementations. Method 1100 can, for example, be used with an example teleoperated system or other control system using a control input device including or coupled to an arm. For example, in some implementations, the control input device is a component of a user control system, e.g., user control system 102 of FIG. 1, and method 1100 can be performed by a control circuit component of the user control system 102. In some examples, the control circuit can include one or more processors, e.g., microprocessors or other circuits, some examples of which are described below with reference to FIG. 12. The control input device can be, for example, any of the control input device and/or arm assembly implementations described herein. Other implementations can use an arm assembly having one or more features described herein with other types of systems, e.g., non-teleoperated systems, a virtual environment (e.g., medical simulation) having no physical manipulator system or slave device and/or no physical subject interacting with a physical manipulator system or slave device, etc.

In block 1102, sensor signals are received. For example, sensor signals can be received as outputs from sensors coupled to one or more members of an arm as described herein. The sensor signals can describe the associated sensors' detection of sensed elements, such as base member 308, first arm member 310, and/or second arm member 312 of FIG. 3, which are moveable in respective rotary degrees of freedom.

In block 1104, the orientations of first arm member 310, second arm member 312, and/or base member 308 are determined based on the sensor signals received in block 1102. For example, rotary sensor signals are processed to determine rotary orientations of the sensed members about their axes of rotation (rotary degrees of freedom).

In block 1106, a first control signal for a first arm motor is received, e.g., first arm motor 322 of FIG. 3. The first control signal can be received from a control circuit of the system, for example, that commands output torque of the first arm motor. In block 1108, the drive shaft of the first arm motor is rotated based on the first control signal, which outputs torque without scaling on the first arm member. For example, as described for FIG. 3, the drive shaft of the first arm motor is coupled directly to the first arm member without a torque transmission mechanism or a torque scaling mechanism positioned therebetween, causing the output of torque on the first arm member without torque scaling. In the example of FIG. 3, the drive shaft of the first arm motor extends along and is rotatable about the axis of rotation of the first arm member, allowing direct driving of the first arm member about the axis by the first arm motor.

In block 1110, a second control signal for a second arm motor is received, e.g., second arm motor 330 of FIG. 3. The second control signal can be received from a control circuit of the system. In block 1112, the drive shaft of the second arm motor is rotated based on the second control signal, which outputs torque without scaling on the second arm member. For example, as described for FIG. 3, the drive shaft of the second arm motor is coupled directly to a pulley without a torque transmission mechanism or a torque scaling mechanism positioned therebetween, allowing the output of torque on the pulley without torque scaling. In the example of FIG. 3, the drive shaft of the second arm motor extends along and is rotatable about the axis of rotation of the pulley. The pulley is coupled to the second arm member by a tension member that transmits the applied torque to the second arm member via another pulley. This allows direct driving by the second arm motor of the second arm member in its rotary degree of freedom about its axis of rotation. In some implementations, as shown in FIG. 3, the drive shaft of the second arm motor extends along and is rotatable about the same axis of rotation of the drive shaft of the first arm motor.

In block 1114, a third control signal for a base motor is received, e.g., base motor 314 of FIG. 3. The third control signal can be received from a control circuit of the system. In block 1116, the drive shaft of the base motor is rotated based on the third control signal, which outputs torque without scaling on the base member. For example, as described for FIG. 3, the drive shaft of the base motor can be coupled directly to the first arm member without a torque transmission mechanism or a torque scaling mechanism positioned therebetween, allowing the output of torque on the base member without torque scaling. In the example of FIG. 3, the drive shaft of the base motor extends along and is rotatable about the axis of rotation of the base member, allowing direct driving of the base member about this axis by the base motor.

It should be noted that the blocks described in the methods disclosed herein can be performed in a different order than shown and/or simultaneously (partially or completely) with other blocks, where appropriate. For example, blocks 1102, 1106, 1110, and/or 1114 can be performed partially or completely simultaneously if different signals are received simultaneously, such that blocks 1104, 1108, 1112, and/or 1116 can be performed partially or completely simultaneously. Further, not all of the described blocks need be performed in various implementations. In some implementations, blocks can be performed multiple times, in different orders, and/or at different times in the methods.

Figure 12:
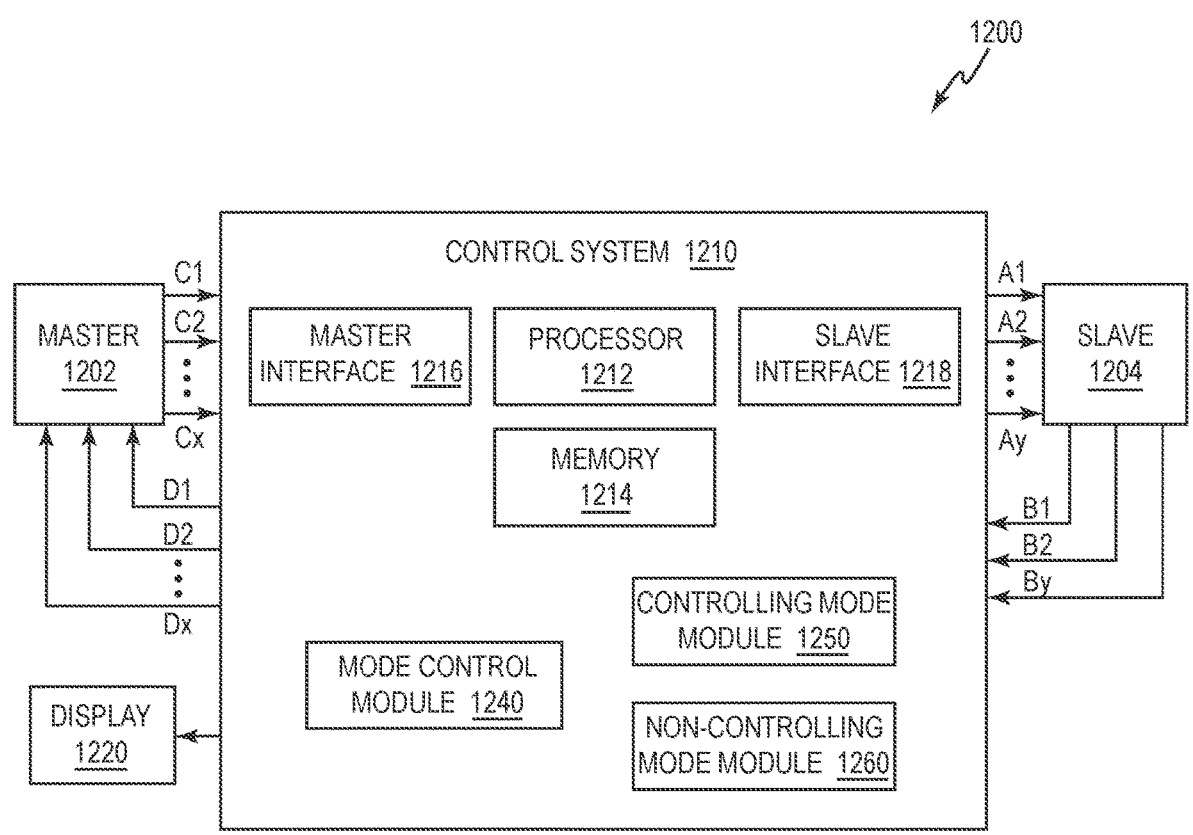
FIG. 12 is a block diagram of an example master-slave system which can be used in one or more implementations described herein.

FIG. 12 is a block diagram of an example master-slave system 1200 which can be used with one or more features described herein. System 1200 includes a master device 1202 that a user may manipulate in order to control a slave device 1204 in communication with the master device 1202. In some implementations, master device 1202 can be, or can be included in, user control system 102 of FIG. 1. In some implementations, slave device 1104 can be, or can be included in, manipulator system 104 of FIG. 1. More generally, master device 1202 can be, or be a portion of, any type of control input device that can be physically manipulated by a user. Master device 1202 generates control signals C1 to Cx indicating positions, states, and/or changes of one or more control input devices in their degrees of freedom. The master device 1202 can also generate control signals (not shown) indicating selection of physical buttons and other manipulations by the user.

A control block 1210 can be included in the master device 1202, in the slave device 1204, or in a separate device, e.g., an intermediary device between master device 1202 and slave device 1204. In some implementations, the control block 1210 can be distributed among multiple of these devices. Control block 1210 receives control signals C1 to Cx and generates actuation signals A1 to Ay, which are sent to slave device 1204. Control block 1210 can also receive sensor signals B1 to By from the slave device 1204 that indicate positions, states, and/or changes of various slave components (e.g., manipulator arm elements). Control block 1210 can include general components such as a processor 1212, memory 1214, and interface hardware 1216 and 1218 for communication with master device 1202 and slave device 1204, respectively. Processor 1212 can execute program code and control basic operations of the system 1200, including functions related to sensing orientations of arm members and sending signals to control motors as described herein, and can include one or more processors of various types, including microprocessors, application specific integrated circuits (ASICs), and other electronic circuits. Memory 1214 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control block 1210, e.g., display(s) 1220 such as the viewer 213 of the user control system 102 and/or display 124 of FIGS. 1 and 2.

In this example, control block 1210 includes a mode control module 1240, a controlling mode module 1250, and a non-controlling mode module 1260. Other implementations can use other modules, e.g., a force output control module, sensor input signal module, etc. In some implementations, the modules 1240, 1250, and 1260 can be implemented using the processor 1212 and memory 1214, e.g., program instructions stored in memory 1214 and/or other memory or storage devices connected to control block 1210.

Mode control module 1240 can detect when a user initiates a controlling mode and a non-controlling mode of the system 1200, e.g., by user selection of controls, sensing a presence of a user at a user control system or control input device, sensing required manipulation of a control input device, etc. The mode control module can set the controlling mode or a non-controlling mode of the control block 1210 based on one or more control signals C1 to Cx.

In some implementations, controlling mode module 1250 may be used to control a controlling mode of control block 1210. Controlling mode module 1250 can receive control signals C1 to Cx and can generate actuation signals A1 to Ay that control actuators of the slave device 1204 and cause it to follow the movement of master device 1202, e.g., so that the movements of slave device 1204 correspond to a mapping of the movements of master device 1202. Controlling mode module 1250 can also be used to control forces on the master device 1202, e.g., torques output on one or more components of the arm assembly of the master device, e.g., base member, arm members, grip members, etc., using one or more control signals D1 to Dx output to actuator(s) used to apply torques to the components, e.g., on arm links of the arm 302, to link members and/or grip members of the control input device 304, etc. In some examples, control signals D1 to Dx can be used to provide force feedback, gravity compensation, etc.

In some implementations, a non-controlling mode module 1260 may be used to control a non-controlling mode of system 1200. In the non-controlling mode, movement in one or more degrees of freedom of master device 1202, or other manipulations of master device 1202, has no effect on the movement of one or more components of slave 1204. In some implementations, non-controlling mode can include one or more other operating modes of the control block 1210, e.g., a selection mode in which movement of the master device 1202 in one or more of its degrees of freedom and/or selection of the control switches of the master device 1202 (e.g., control switches 1050 of FIG. 10) can control selection of displayed options, e.g., in a graphical user interface displayed by display 1220 and/or other display device. A viewing mode can allow movement of the master device 1202 to control a display provided from cameras, or movement of cameras, that may not be included in the slave device 1204. Control signals C1 to Cx can be used by the non-controlling mode module 1260 to control such elements (e.g., cursor, views, etc.) and control signals D1 to Dx can be determined by the non-controlling mode module to cause output of torques on the master device 1202 during such non-controlling modes, e.g., to indicate to the user interactions or events occurring during such modes.

Some implementations described herein, e.g., method 1100, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A mechanical arm assembly comprising:
   a base member rotatable about a base axis;
   a first arm member including a first portion and a second portion, the first arm member being rotatably coupled to the base member at the first portion of the first arm member, and the first arm member being rotatable with respect to the base member about a first axis that is orthogonal to the base axis;
   a first motor coupled to the base member, the first motor including a first drive shaft rotatable about the first axis and coupled to the first arm member;
   a second arm member including a first portion and a second portion, the first portion of the second arm member being rotatably coupled to the second portion of the first arm member, and the second arm member being rotatable with respect to the first arm member about a second axis the second axis parallel to the first axis;
   a second motor coupled to the base member, the second motor including a second drive shaft rotatable about the first axis and coupled to the second arm member;
   a grip member coupled to the second portion of the second arm member; and a third motor coupled to a support, the third motor including a third drive shaft rotatable about the base axis and coupled to the base member.

2. The mechanical arm assembly of claim 1, wherein:
the first portion of the first arm member is a first end of the first arm member;
the second portion of the first arm member is a second end of the first arm member;
the first portion of the second arm member is a first end of the second arm member, and;
the second portion of the second arm member is a second end of the second arm member.

3. The mechanical arm assembly of claim 1, wherein the first motor is configured to rotate the first drive shaft and output torque on the first arm member about the first axis.

4. The mechanical arm assembly of claim 1, wherein a 1:1 drive ratio of torque is provided from the first motor to the first arm member.

5. The mechanical arm assembly of claim 1, wherein the first drive shaft is directly coupled to the first arm member.

6. The mechanical arm assembly of claim 1, further comprising:
a first sensor coupled to the first drive shaft; and
a second sensor coupled to the second drive shaft.

7. The mechanical arm assembly of claim 1, wherein the second motor is configured to rotate the second drive shaft and output torque on the second arm member about the second axis.

8. The mechanical arm assembly of claim 1, further comprising a force transmission mechanism coupled between the second drive shaft and the second arm member.

9. The mechanical arm assembly of claim 8, wherein:
the force transmission mechanism includes a drive pulley and a tension element;
the drive pulley is coupled to the second drive shaft;
the tension element is coupled between the drive pulley and the second arm member;
the tension element extends along a length of the first arm member and is coupled to a second pulley;
the second pulley is coupled to the second arm member; and
the second pulley is rotatable about the second axis.

10. The mechanical arm assembly of claim 1, wherein the first drive shaft is part of a rotor of the first motor.

11. The mechanical arm assembly of claim 1, wherein a 1:1 drive ratio of torque is provided from the second motor to the second arm member.

12. The mechanical arm assembly of claim 1, wherein a 1:1 drive ratio of torque is provided from the third motor to the base member.

13. The mechanical arm assembly of claim 1, wherein the grip member is movable in one or more degrees of freedom provided by rotation of the first arm member and the second arm member about the first and second axes, respectively.

14. The mechanical arm assembly of claim 1, wherein the mechanical arm assembly is included in a teleoperated surgical system.

15. A mechanical arm assembly comprising:
a base member rotatable about a base axis;
a first arm member including a first portion and a second portion, the first portion of the first arm member being rotatably coupled to the base member, and the first arm member being rotatable with respect to the base member about a first axis that is orthogonal to the base axis;
a first motor coupled to the base member, the first motor including a first drive shaft coupled to the first arm member, the first drive shaft being rotatable about the first axis;
a second arm member including a first portion and a second portion, the first portion of the second arm member being rotatably coupled to the second portion of the first arm member, and the second arm member being rotatable about a second axis that extends parallel to the first axis;
a second motor coupled to the base member, the second motor including a second drive shaft rotatable about the first axis, and the second drive shaft being coupled to the second arm member;
a first rotary sensor coupled to the first drive shaft and configured to detect an orientation of the first arm member about the first axis;
a second rotary sensor coupled to the second drive shaft and configured to detect an orientation of the second arm member about the second axis;
a grip member coupled to the second portion of the second arm member and movable in one or more degrees of freedom provided by rotation of the first arm member or the second arm member; and
a third motor coupled to a support, the third motor including a third drive shaft rotatable about the base axis and coupled to the base member.

16. The mechanical arm assembly of claim 15, wherein:
the mechanical arm assembly further comprises a force transmission mechanism coupled between the second drive shaft and the second arm member;
the force transmission mechanism includes a drive pulley and a tension element;
the drive pulley is coupled to the second drive shaft; and
the tension element is coupled between the drive pulley and the second arm member.

* * * * *